United States Patent
Butz et al.

(10) Patent No.: US 11,235,147 B2
(45) Date of Patent: *Feb. 1, 2022

(54) CHARGE BALANCING CIRCUIT, STIMULATOR CIRCUIT AND METHOD FOR CHARGE BALANCING

(71) Applicant: Albert-Ludwigs-Universität Freiburg, Freiburg (DE)

(72) Inventors: Natalie Butz, Bad Krozingen (DE); Matthias Kuhl, Freiburg (DE); Yiannos Manoli, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 571 days.

This patent is subject to a terminal disclaimer.

(21) Appl. No.: 16/217,432

(22) Filed: Dec. 12, 2018

(65) Prior Publication Data

US 2019/0111249 A1 Apr. 18, 2019

Related U.S. Application Data

(63) Continuation-in-part of application No. 15/173,380, filed on Jun. 3, 2016, now Pat. No. 10,166,399.

(30) Foreign Application Priority Data

Jun. 3, 2015 (EP) .................................. 15170554

(51) Int. Cl.
*A61N 1/08* (2006.01)
*A61N 1/02* (2006.01)
*A61N 1/37* (2006.01)

(52) U.S. Cl.
CPC ............... *A61N 1/08* (2013.01); *A61N 1/025* (2013.01); *A61N 1/3706* (2013.01)

(58) Field of Classification Search
CPC . A61N 1/05; A61N 1/08; A61N 1/025; A61N 1/3706; A61N 1/3782
See application file for complete search history.

(56) References Cited

U.S. PATENT DOCUMENTS

| | | | |
|---|---|---|---|
| 6,035,237 | A | 3/2000 | Schulman et al. |
| 2012/0116483 | A1 | 5/2012 | Yonezawa et al. |
| 2012/0197356 | A1 | 8/2012 | Wei et al. |
| 2013/0204319 | A1 | 8/2013 | Trier et al. |

FOREIGN PATENT DOCUMENTS

WO 03090849 A1 11/2003

*Primary Examiner* — Mallika D Fairchild
(74) *Attorney, Agent, or Firm* — Slater Matsil, LLP

(57) ABSTRACT

A charge balancing circuit is adapted to be connected to an electrode and to a stimulation source. The charge balancing circuit has an electrode terminal for receiving an electrode voltage, an amplifier coupled to the electrode terminal and adapted to amplify and invert the electrode voltage for generating an intermediate voltage and a compensation stage. The compensation stage is adapted to generate an output current if the electrode voltage lies outside a specified safety range and to generate the output current depending on the intermediate voltage. The compensation stage is further adapted to supply the output current to the electrode terminal for driving the electrode voltage towards and/or into the safety range.

18 Claims, 7 Drawing Sheets

FIG. 8
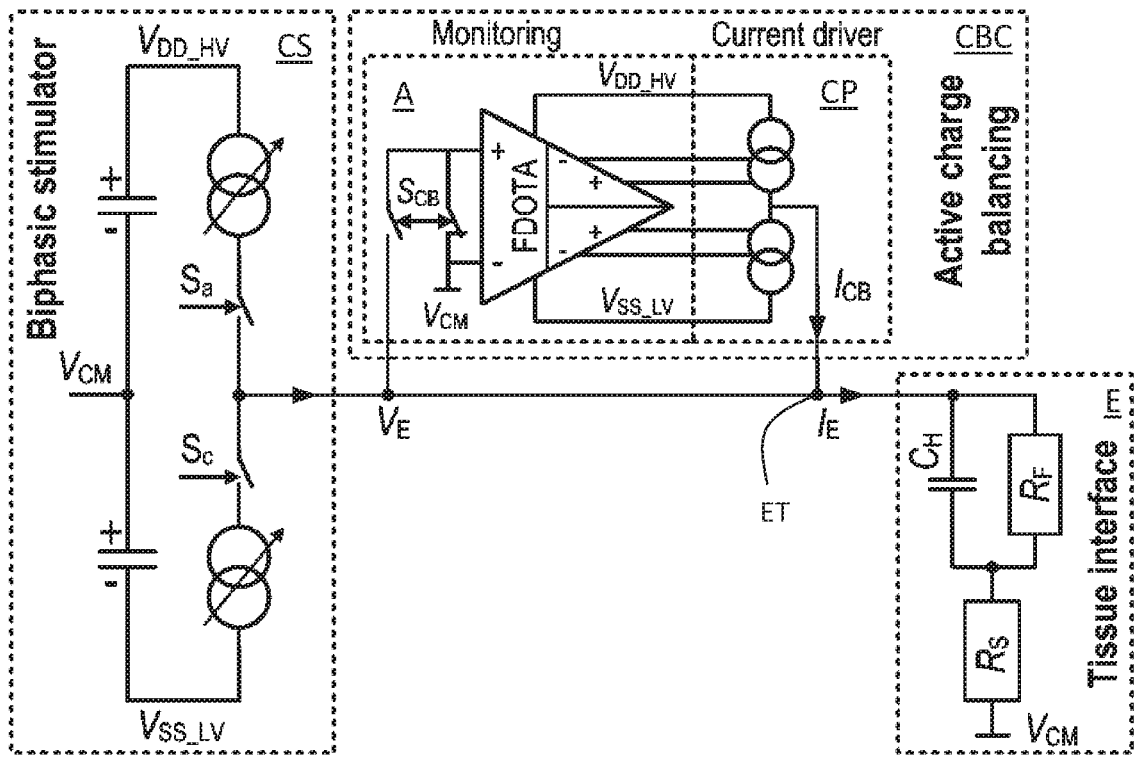
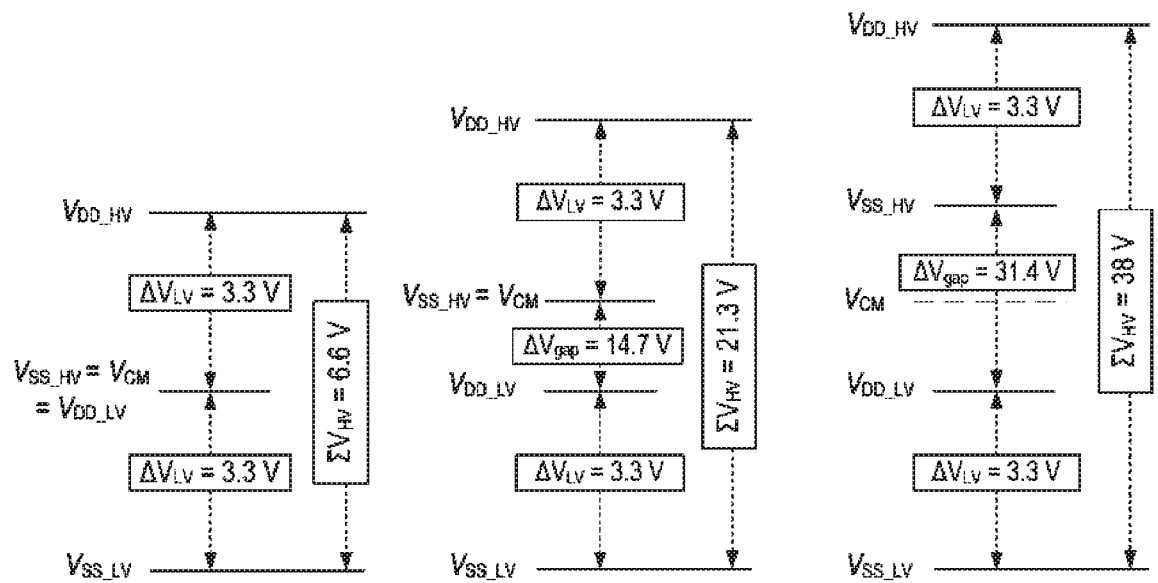
FIG. 9A   FIG. 9B   FIG. 9C

CHARGE BALANCING CIRCUIT, STIMULATOR CIRCUIT AND METHOD FOR CHARGE BALANCING

CROSS-REFERENCE TO RELATED APPLICATIONS

This application is a continuation-in-part of U.S. application Ser. No. 15/173,380, filed on Jun. 3, 2016, which claims priority to European Patent Application No. 15170554.8, filed on Jun. 3, 2015, which applications are hereby incorporated herein by reference.

TECHNICAL FIELD

The present disclosure relates to a charge balancing circuit, a stimulator circuit and a method for charge balancing, in particular for functional electrical stimulation of biological tissue.

BACKGROUND

Functional electrical stimulation may be used for stimulating muscles or nerves by electrical charge. To this end, electrodes may be in direct contact with biologic tissue and a charge may be brought on the electrode for example by a current source, a voltage source or by capacitive discharge. Fields of applications comprise, for example, cardiac pacemakers, cochlear and retinal implants, peripheral nerve and muscle stimulators, deep brain stimulators and arrangements for restoring tactile sense of amputees. To guarantee safe stimulation, electrode and tissue destructions have to be prevented. Concerning safety aspects, charge balancing may be one major issue, since charge accumulation over time may harm the tissue and lead to electrolysis which may dissolve the electrode.

After a stimulating pulse, residual charge may remain at the electrode. Therefore, charge balancing may be necessary in order to keep the residual charge and the corresponding electrode voltage within a safety range. Existing concepts for charge balancing may have disadvantages as for example with respect to their power consumption, complexity, required space and response time.

SUMMARY

The present disclosure provides an improved concept for charge balancing for functional electrical stimulation of biological tissue that allows for decreased power consumption, complexity, required space and response time.

In one embodiment, a charge balancing circuit is adapted to be connected to an electrode and to a stimulation source. The charge balancing circuit has an electrode terminal for receiving an electrode voltage, an amplifier coupled to the electrode terminal and adapted to amplify and invert the electrode voltage for generating an intermediate voltage and a compensation stage. The compensation stage is adapted to generate an output current if the electrode voltage lies outside a specified safety range and to generate the output current depending on the intermediate voltage. The compensation stage is further adapted to supply the output current to the electrode terminal for driving the electrode voltage towards and/or into the safety range.

In another embodiment, a charge balancing circuit is adapted to be connected to an electrode and to a stimulation source, the stimulation source configured to provide a stimulus to the electrode for functional electrical stimulation of biological tissue. The charge balancing circuit comprises an electrode terminal for receiving an electrode voltage, a reference terminal for receiving a reference voltage, a differential amplifier and a compensation stage. The differential amplifier is coupled to the electrode terminal and to the reference terminal and is adapted to amplify and invert a difference between the electrode voltage and the reference voltage for generating a first pair of differential voltage signals and a second pair of differential voltage signals having a lower voltage level than the first pair. The compensation stage is implemented as a transistor stage with at least two transistor pairs connected in series between a first and a second supply terminal. The compensation stage is adapted to generate, if the electrode voltage lies outside a specified safety range, an output current by controlling the at least two transistor pairs with the first and the second pair of differential voltage signals, and to supply the output current to the electrode terminal for driving the electrode voltage towards and/or into the safety range.

BRIEF DESCRIPTION OF THE DRAWINGS

In the following, the invention is explained in detail with the aid of exemplary implementations by reference to the drawings. Components that are functionally identical or have an identical effect may be denoted by identical references. Identical components and/or components with identical effects may be described only with respect to the figure where they occur first; their description is not necessarily repeated in subsequent figures.

In the drawings:

FIG. 8 shows a further exemplary implementation of a stimulator circuit according to the improved concept;

FIG. 9, which includes FIGS. 9A-9C, shows a representation of an adaptive quad-rail system;

DETAILED DESCRIPTION OF ILLUSTRATIVE EMBODIMENTS

Figure 1:
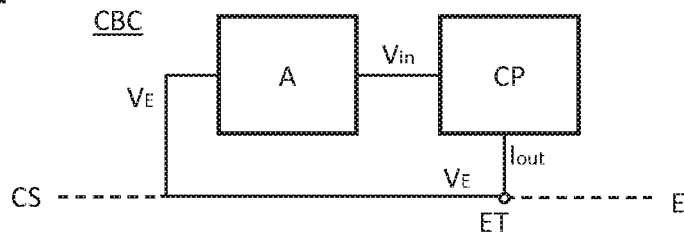
FIG. 1 shows an exemplary implementation of a charge balancing circuit according to the improved concept.

Embodiments of the present invention will be described in text. Specific implementations will then be discussed with reference to the drawings.

According to embodiments of the invention, an electrode voltage that may remain at an electrode for functional electrical stimulation of biological tissue after a stimulus has been provided to the electrode by a stimulation source is amplified and inverted for generating an intermediate voltage. Based on the intermediate voltage, an output current is generated if the electrode voltage lies outside a specified safety range. The output current is then used to drive the electrode voltage towards and/or into the safety range. In this way, it may be ensured that the electrode voltage does not stay outside the safety range long enough to cause damage of the biological tissue or the electrode.

According to embodiments of the invention, a charge balancing circuit is provided. The charge balancing circuit is adapted to be connected to an electrode and to a stimulation source, wherein the stimulation source is configured to provide a stimulus to the electrode for functional electrical stimulation of biological tissue. The stimulus can be for example a monophasic or a biphasic stimulus.

The charge balancing circuit comprises an electrode terminal for receiving an electrode voltage, an amplifier coupled to the electrode terminal and adapted to amplify and invert the electrode voltage for generating an intermediate voltage and a compensation stage. The compensation stage is implemented as a transistor stage with at least a first transistor and adapted to generate an output current if the electrode voltage lies outside a specified safety range. To this end, the compensation stage is adapted to generate the output current depending on the intermediate voltage by controlling a conductance at least of the first transistor. The compensation stage is further adapted to supply the output current to the electrode terminal for driving the electrode voltage towards and/or into the safety range.

The amplification and inversion of the electrode voltage by the amplifier may for example correspond to an amplification and inversion of a voltage difference between the electrode voltage and a reference voltage.

The stimulation source is for example connected to the electrode, while the electrode may be connected to the biological tissue. The electrode terminal is for example arranged between the stimulation source and the electrode. The stimulation source may for example be implemented as a current source, a voltage source or a source for capacitive discharge. The stimulus may for example be provided by the stimulation source to the electrode in the form of a current or voltage pulse causing the electrode voltage at the electrode terminal.

The output current may assume different polarities or directions of current. In particular, the output current may be supplied to the electrode terminal in either direction. That is, a current may flow from the compensation stage to the electrode terminal or vice versa. The polarity of the output current depends on whether the electrode voltage lies above or below the safety range. In particular, if the electrode voltage lies above the safety range the polarity of the output current is such that the electrode voltage is decreased. Analogously, the polarity of the output current is such that the electrode voltage is increased if the electrode voltage lies below the safety range. The correct polarity of the output current is ensured for example by the inversion of the electrode voltage and by the implementation of the compensation stage.

The safety range may for example be predetermined by an application of the functional electrical stimulation. The safety range may correspond to a range of voltages and corresponding charges that are known not to damage the biological tissue and the electrode when applied permanently or during an extended period to the electrode and the electrode terminal, respectively. If the electrode voltage lies outside of the safety range, the driving of the electrode voltage into the safety range by means of the output current may avoid a damage of the biological tissue and the electrode.

The safety range may for example correspond to an interval of voltages and corresponding charges that lies symmetrically around the reference voltage. The reference voltage may for example be a common mode voltage. The reference voltage may correspond to an electrical potential of the electrode, in particular to an electrical potential of the biological tissue in case the electrode is connected to the biological tissue.

The compensation stage being implemented as a transistor stage means that the main functionality of the compensation stage, that is the generation and supply of the output current, is performed by controlling one or more transistors including the first transistor. Controlling the conductance at least of the first transistor may for example correspond to controlling at least the first transistor as a switch, in particular as an open or closed switch depending on the intermediate voltage.

According to the improved concept, the safety range is encoded in characteristic values of components comprised by the amplifier and the compensation stage. In particular, an external definition of the safety range is not necessary according to the improved concept. Consequently, a charge balancing circuit according to the improved concept may reduce a power consumption a space required by the charge balancing circuit.

According to at least one implementation of the charge balancing circuit, the compensation stage comprises a first transistor being coupled between a first supply terminal and the electrode terminal for supplying the output current to the electrode terminal. A control terminal of first transistor is coupled to the amplifier for receiving the intermediate voltage.

In some implementations, the first transistor is implemented as a bipolar transistor. In this case, for example an emitter terminal of the first transistor is coupled to the electrode terminal and a collector terminal of the first transistor is coupled to the first supply terminal. The control terminal of the first transistor is then for example a base terminal.

In other implementations, the first transistor is implemented as a field effect transistor, for example a metal oxide semiconductor, MOS, transistor. In particular, the first transistor may be implemented as a high voltage field effect transistor. In such implementations, a drain terminal and a source terminal of the first transistor are for example coupled to the first supply terminal and the electrode terminal, respectively. The control terminal of the first transistor is then for example a gate terminal.

Depending on the intermediate voltage, the first transistor can for example act as an open or a closed switch. In particular, the first transistor may act as a closed switch if the electrode voltage lies above the safety range and as an open switch if the electrode voltage lies within the safety range or below the safety range. In such implementations, the first transistor may for example be implemented as a p-channel field effect transistor, for example as a p-channel enhancement MOS transistor. Such implementations may be for example advantageous, if it can be ensured that the electrode voltage may only lie within the safety range or above the safety range but not below the safety range. This may for example be the case if the stimulus is a monophasic stimulus and has a polarity causing only an increase of the electrode voltage but not a decrease.

Alternatively, the first transistor may act as a closed switch if the electrode lies below the safety range and as an open switch if the electrode voltage lies within the safety range or above the safety range. In such implementations, the first transistor may for example be implemented as an n-channel field effect transistor. Such implementations may for example be advantageous, if it can be ensured that the electrode voltage may only lie within the safety range or below the safety range but not above the safety range. This may for example be the case if the stimulus is a monophasic stimulus and has a polarity causing only a decrease of the electrode voltage but not an increase.

Acting as a closed switch, the output current may be supplied to the electrode terminal for driving the electrode voltage towards and/or into the safety range. Acting as an open switch, no current or only a strongly reduced current may be supplied from the first supply terminal to the electrode terminal.

According to at least one implementation of the charge balancing circuit, an amplification factor of the amplifier is chosen such that at least one threshold condition for the first transistor is met when the electrode voltage is equal or approximately equal to at least one boundary of the safety range.

The threshold condition for the first transistor may for example correspond to a threshold value for a base-emitter voltage, if the first transistor is implemented as a bipolar transistor. The threshold condition for the first transistor may for example correspond to a threshold gate voltage, for example a threshold gate-source voltage, if the first transistor is implemented as a field effect transistor.

The at least one boundary of the safety range may for example be an upper boundary of the safety range. In this case, the first transistor may act as an open switch if the electrode voltage lies below the upper boundary, and as a closed switch otherwise. This is achieved by choosing the amplification factor accordingly, such that the intermediate voltage coupled to the control terminal of the first transistor renders the first transistor conducting whenever the electrode voltage is equal or above the upper boundary. The polarity of a first supply voltage applied at the first supply terminal is chosen accordingly to result in the output current decreasing the electrode voltage when the first transistor is conducting.

The at least one boundary of safety range may for example be a lower boundary of the safety range. In this case, the first transistor may act as an open switch if the electrode voltage lies above the lower boundary and as a closed switch otherwise. This is achieved by choosing the amplification factor accordingly, such that the intermediate voltage coupled to the control terminal of the first transistor renders the first transistor conducting whenever the electrode voltage is equal or below the lower boundary. The polarity of a first supply voltage applied at the first supply terminal is chosen accordingly to result in the output current increasing the electrode voltage when the first transistor is conducting.

According to at least one implementation of the charge balancing circuit, the compensation stage is implemented as a push-pull stage comprising the first transistor and a second transistor. The first and the second transistor are implemented complementary to each other and coupled in series between a first and a second supply terminal for generating the output current. The compensation stage is adapted to generate the output current by controlling the conductance of the first transistor and a conductance of the second transistor.

According to at least one implementation of the charge balancing circuit, the electrode terminal is connected between the first and the second transistor and control terminals of the first and the second transistor are coupled to the amplifier for receiving the intermediate voltage.

In some implementations, the first and the second transistor are implemented as bipolar transistors. In this case, for example collector terminals of the first and second transistor are coupled to the first and the second supply terminal, respectively, and emitter terminals of the first and second transistor are coupled to the electrode terminal. The control terminals of the first and second transistor are then for example base terminals.

In other implementations, the first and the second transistor are implemented as field effect transistors, for example as MOS transistors. In particular, the first and the second transistor may be implemented as a high voltage field effect transistor. In such implementations, drain terminals of the first and second transistor are coupled to the first and second supply terminal, respectively, while source terminals of the first and second transistor are coupled to the electrode terminal. The control terminals of the first and second transistor are then for example respective gate terminals.

Depending on the intermediate voltage, the first and the second transistor can for example act as open or closed switches. For example, the first transistor may be implemented as an n-channel field effect transistor, for example as an n-channel enhancement MOS transistor. Then, the second transistor may for example be implemented as a p-channel field effect transistor, for example as a p-channel enhancement MOS transistor.

In such implementations, the first transistor may act as an open switch if the electrode voltage lies above the lower boundary of the safety range and as a closed switch otherwise. Analogously, the second transistor may act as an open switch if the electrode voltage lies below the upper boundary of the safety range and as a closed switch otherwise. Such implementations may be particularly advantageous, if the stimulus is a biphasic stimulus or a monophasic stimulus.

In this way, by choosing the polarity of the first supply voltage accordingly, an output current increasing the electrode voltage may be generated if the electrode voltage lies below the safety range by the first transistor acting as a closed switch and the second transistor acting as an open switch. Analogously, by choosing a polarity of a second supply voltage applied at the second supply terminal accordingly, an output current decreasing the output voltage may be generated if the electrode voltage lies above the safety range by the first transistor acting as an open switch and the second transistor acting as a closed switch.

In either case, the output current may be supplied to the electrode terminal for driving the electrode voltage towards and/or into the safety range.

According to at least one implementation of the charge balancing circuit, an amplification factor of the amplifier is chosen such that at least one threshold condition for the first and/or the second transistor is met when the electrode voltage is equal or approximately equal to at least one boundary of the safety range.

The at least one threshold condition may for example correspond to a threshold value for a base-emitter voltage, if the first and/or the second transistor are implemented as bipolar transistors. The at least one threshold condition may for example correspond to a threshold voltage, for example a threshold gate-source voltage, of the first and/or the second transistor, if the first and/or the second transistor are implemented as field effect transistors.

In particular, the amplification factor may be chosen such that a first threshold condition for the first transistor is met when the electrode voltage is equal or approximately equal to a first boundary of the safety range. Alternatively, in addition or at the same time, the amplification factor may be chosen such that a second threshold condition for the second transistor is met when the electrode voltage is equal or approximately equal to a second boundary of the safety range.

The first boundary may for example correspond to the lower boundary of the safety range, while the second boundary may for example correspond the upper boundary of the safety range. The first threshold condition may then for example correspond to a threshold voltage of the first transistor and the second threshold condition may for example correspond to a threshold voltage of the second transistor. Therein, the first and the second threshold condition may depend on characteristics of the first and second transistor, respectively. The characteristics may include spatial dimensions and/or material properties of the first and the second transistor. If the first and the second transistor are implemented as MOS transistors, the characteristics may for example include an aspect ratio of a gate and/or a specific capacity of gate capacitors of the first and the second transistor.

The first transistor may act as an open switch if the electrode voltage lies above the lower boundary, and as a closed switch otherwise. The second transistor may act as an open switch if the electrode voltage lies below the upper boundary, and as a closed switch otherwise. This is achieved by choosing the amplification factor accordingly, such that the intermediate voltage coupled to the control terminal of the first transistor renders the first transistor conducting whenever the electrode voltage is equal or below the lower boundary. Analogously, the amplification factor is chosen accordingly, such that the intermediate voltage coupled to the control terminal of the second transistor renders the second transistor conducting whenever the electrode voltage is equal or above the upper boundary.

According to at least one implementation of the charge balancing circuit, the compensation stage comprises at least one current limiting component coupled between the first transistor and the first supply terminal and/or between the second transistor and the second supply terminal.

The at least one current limiting component may for example be implemented as a resistor, in particular as a tunable resistor, for example a digitally tunable resistor, for example a digital potentiometer.

By means of the at least one current limiting component an upper limit for the output current may be defined depending on at least one resistance value of the at least one current limiting component.

In some implementations, the compensation stage comprises a first and a second current limiting component. The first current limiting component is coupled between the first supply terminal and the first transistor, while the second current limiting component is coupled between the second supply terminal and the second transistor. The first and the second transistor may be coupled to the first and the second current limiting component, respectively, by their drain terminals. By this arrangement, a drain potential of the first and the second transistor may be reduced. Consequently, it may be achieved that the first and/or the second transistor do not operate in a saturation regime of operation when the output current is generated. In particular, the first and/or the second transistor may be forced to stay in linear regime of operation by causing pinch off. Thereby, the output current may be effectively limited to a maximum value.

According to at least one implementation of the charge balancing circuit, the compensation stage comprises at least one further current limiting component coupled between the first transistor and the electrode terminal and/or between the second transistor and the electrode terminal.

The at least one further current limiting component may for example be implemented as a resistor, in particular as a tunable resistor, for example a digitally tunable resistor, for example a digital potentiometer.

By means of the at least one further current limiting component an upper limit for the output current may be defined depending on at least one resistance value of the at least one further current limiting component.

In some implementations, the compensation stage comprises a first and a second further current limiting component. The first further current limiting component is coupled between the first transistor and the electrode terminal, while the second further current limiting component is coupled between the second transistor and the electrode terminal. The first and the second transistor may be coupled to the electrode terminal by their source terminals. By this arrangement, a source potential of the first and the second transistor may be reduced. Consequently, source degeneration may be used to limit the output current effectively to a maximum value for example by influencing the slope of the current output curve.

According to at least one implementation of the charge balancing circuit, the compensation stage comprises a third transistor coupled between the first transistor and the electrode terminal, wherein a control terminal of the third transistor is connected to a first bias voltage.

According to at least one implementation of the charge balancing circuit, the compensation stage comprises the third transistor and the first further current limiting component, wherein the first further current limiting component is coupled in series between the first transistor and the third transistor.

According to at least one implementation of the charge balancing circuit, the compensation stage comprises a fourth transistor coupled between the second transistor and the electrode terminal, wherein a control terminal of the fourth transistor is connected to an additional bias voltage. The additional bias voltage may be equal to the first bias voltage.

According to at least one implementation of the charge balancing circuit, the compensation stage comprises the fourth transistor and the second further current limiting component, wherein the second further current limiting component is coupled in series between the second transistor and the fourth transistor.

In several implementations, the third and/or the fourth transistor are implemented as field effect transistors, for example MOS transistors. In several implementations, the third and the fourth transistor are implemented complementary to each other. The third transistor may be implemented complementary to the first transistor, the fourth transistor may be implemented complementary to the second transistor.

The third and/or the fourth transistor may for example be used to compensate an asymmetry between the first and the second transistor. The third and/or the fourth transistor may also be used for shielding the first and/or second transistor for example with respect to the electrode voltage.

According to at least one implementation of the charge balancing circuit, the compensation stage further comprises a first and a second protection transistor coupled in series between the intermediate voltage and a second bias voltage. Therein, a control terminal of the first protection transistor is coupled to the second bias voltage, a control terminal of the second protection transistor is coupled to the intermediate voltage and the control terminal of the first transistor is connected between the first and the second protection transistor.

In such implementations, the first and the second protection transistor may for example select one of the intermediate voltage and the second bias voltage. In particular, the first and the second protection transistor may select the highest voltage or the lowest voltage of the intermediate voltage and the second bias voltage. The control terminal of the first transistor is connected to the selected voltage in this way, such that a protection of the first transistor from too high voltage values of the intermediate voltage may be achieved. In several implementations, the second bias voltage is equal to the first bias voltage.

According to at least one implementation of the charge balancing circuit, the compensation stage further comprises a third and a fourth protection transistor coupled in series between the intermediate voltage and a third bias voltage. Therein, a control terminal of the third protection transistor is coupled to the third bias voltage, a control terminal of the fourth protection transistor is coupled to the intermediate voltage and the control terminal of the second transistor is connected between the third and the fourth protection transistor.

In such implementations, the third and the fourth protection transistor may for example select one of the intermediate voltage and the third bias voltage. In particular, the third and the fourth protection transistor may select the highest voltage or the lowest voltage of the intermediate voltage and the third bias voltage. In particular, in implementations comprising the first and the second protection transistor and wherein the first and the second protection transistor select the highest of the intermediate voltage and the second bias voltage, the third and the fourth protection transistor may select the lowest of the intermediate voltage and the third bias voltage, or vice versa. The control terminal of the second transistor is connected to the voltage selected by the third and the fourth protection transistor in this way, such that a protection of the second transistor from too high voltage values of the intermediate voltage may be achieved. In several implementations, the third bias voltage is equal to the second bias voltage and/or to the first bias voltage.

According to at least one implementation of the charge balancing circuit, the amplifier comprises an operational amplifier connected as an inverting amplifier.

According to at least one implementation of the charge balancing circuit, the amplifier comprises an operational amplifier, a first resistive element and a second resistive element. The first resistive element is connected to a first input of the operational amplifier and to the electrode terminal for receiving the electrode voltage. The second resistive element is connected between the first input of the operational amplifier and an output of the operational amplifier. The operational amplifier further has a second input connected to the reference voltage.

The first and/or the second resistive element may for example be implemented as resistors. From the described arrangement of the operational amplifier, the first and the second resistive element, it follows that the electrode voltage, in particular a difference between the electrode voltage and the reference voltage is inverted and amplified by an amplification factor given by a ratio of a resistance value of the second resistive element and a resistance value of the first resistive element.

According to at least one implementation of the charge balancing circuit, the resistance value of the first resistive element and/or the resistance value of the second resistive element is adjustable for adjusting the amplification factor of the amplifier.

In such implementations, the amplification factor may be adjusted for example in order to realize different safety ranges for example corresponding to different applications of the functional electrical stimulation and the charge balancing circuit, respectively.

According to at least one implementation of the charge balancing circuit, the charge balancing circuit further comprises a switch arrangement configured to connect the amplifier to the electrode terminal during an operating mode of operation of the charge balancing circuit and to disconnect the amplifier from the electrode terminal during a pause mode of operation of the charge balancing circuit.

The pause mode of operation may for example correspond to a time period during which the stimulation source provides the stimulus to the electrode. The operating mode may for example lie within or correspond to a time period during which the stimulation source does not provide the stimulus to the electrode.

According to at least one implementation of the charge balancing circuit, the switch arrangement is further configured to connect the first and the second input of the operational amplifier during the pause mode and to disconnect the first and the second input of the operational amplifier from each other during the operating mode. In this way, it may for example be ensured that the intermediate voltage drops to zero or approximately to zero during the pause mode.

According to the improved concept also a stimulator circuit for functional electrical stimulation is provided. The stimulator circuit comprises a charge balancing circuit according to the improved concept and the stimulation source. The stimulation source is implemented as a current source, connected to the electrode terminal of the charge balancing circuit and configured to supply a monophasic and/or a biphasic current pulse to the charge balancing circuit via the electrode terminal. Therein, the current pulse may for example correspond to the stimulus provided to the electrode by the stimulation source.

According to at least one implementation of the stimulator circuit, the stimulator circuit further comprises the electrode. Therein, the electrode is connected to the electrode terminal for receiving the electrode voltage and the current pulse.

According to at least one implementation of the stimulator circuit, the current source is connected to the first supply terminal for supplying current of a first polarity to form a first part of the current pulse. Furthermore, the current source is connected to the second supply terminal for supplying current of a second polarity to form a second part of the current pulse.

This means, in implementations of the stimulator circuit, wherein the compensation stage comprises the first and/or the second transistor, the output current is generated based on the same voltage supply as the current pulse generated and supplied by the current source. This allows for a particularly compact design of the stimulator circuit, since no additional or external voltage supply is necessary for the compensation stage.

Further implementations of the stimulator circuit are readily derived from the various implementations of the charge balancing circuit and vice versa.

The first and the second polarity of the current supplied by the current source correspond to directions of current. In particular, if the first polarity corresponds to a positive current from the current source to the electrode, the second polarity corresponds to a negative current from the current source to the electrode or to a positive current from the electrode to the current source, respectively. Analogously, if the first polarity corresponds to a negative current from the current source to the electrode or a positive current from the electrode to the current source, the second polarity corresponds to a positive current from the current source to the electrode.

The first and the second part of the current pulse may correspond to complementarity current pulses, in particular to current pulses with the same or approximately the same pulse width and opposite sign. The first and the second part of the current pulse may for example correspond to rectangular or approximately rectangular current pulses. Alternatively, also other shapes of the first and the second part of the current pulse are possible. In particular sinusoidal or approximately sinusoidal shapes are possible.

According to the improved concept also a method for charge balancing for functional electrical stimulation of biological tissue is provided. The method comprises receiving an electrode voltage and generating an intermediate voltage by amplifying and inverting the electrode voltage. Furthermore, the method comprises determining whether the electrode voltage lies outside a specified safety range and, if the electrode voltage lies outside the safety range, generating, depending on the intermediate voltage, an output current for driving the electrode voltage towards and/or into the safety range by controlling a conductance at least of a first transistor.

According to at least one implementation of the method, an amplification factor of the electrode voltage is chosen such that at least one threshold condition for the generation of the output current is met when the electrode voltage is equal or approximately equal to at least one boundary of the safety range.

Further implementations of the method are readily derived from the various implementations of the charge balancing circuit and the stimulator circuit and vice versa.

FIG. 1 shows an exemplary implementation of a charge balancing circuit CBC according to the improved concept. The charge balancing circuit CBC comprises an electrode terminal ET that can be connected to a current source CS and to an electrode E. The charge balancing circuit CBC further comprises an amplifier A connected to the electrode terminal ET and a compensation stage CP connected to the electrode terminal ET and to the amplifier A.

At the electrode terminal ET an electrode voltage $V_E$ may be applied. The electrode voltage $V_E$ may result from a current pulse that may be supplied from the current source CS to the electrode E and to the charge balancing circuit CBC, when the current source CS and the electrode E are connected to the charge balancing circuit CBC. In particular, the electrode voltage $V_E$ may be applied during the current pulse being supplied but also after the current pulse has been supplied or between two successive current pulses being supplied. The electrode voltage $V_E$ may also correspond to an excess voltage remaining at the electrode E and the electrode terminal ET after a monophasic current pulse or an unbalanced biphasic current pulse has been supplied from the current source CS.

The electrode E may for example be connected to the biological tissue, for example of a human body. The current pulse may then for example serve for functional electrical stimulation of the biological tissue.

The amplifier A is configured to invert and amplify the electrode voltage $V_E$, in particular to invert and amplify a voltage difference between the electrode voltage $V_E$ and a reference voltage $V_{CM}$. The reference voltage $V_{CM}$ may for example be a common mode voltage, for example the reference voltage $V_{CM}$ may correspond to a potential of the biological tissue to which the electrode E may be connected.

The amplifier A generates an intermediate voltage $V_{in}$ by means of said inversion and amplification and supplies the intermediate voltage $V_{in}$ to the compensation stage CP. If the electrode voltage $V_E$ lies outside a specified safety range, the intermediate voltage $V_{in}$ may lie outside a voltage window derived from the safety range. In particular, the voltage window may be derived from the safety range by multiplying boundary values of the safety range by an amplification factor of the amplifier A. If the electrode voltage $V_E$ lies outside the safety range, and as a consequence the intermediate voltage $V_{in}$ lies outside the voltage window, the compensation stage CP generates an output current $I_{out}$ depending on the intermediate voltage $V_{in}$ and supplies the output current $I_{out}$ to the electrode terminal ET. Therein, the output current $I_{out}$ is generated such that the electrode voltage $V_E$ is driven towards and/or into the safety range.

In this way it may be achieved that the electrode voltage $V_E$ remains outside the safety range only for a limited time, such that a damage of the biological tissue and/or the electrode E may be avoided.

Figure 2:
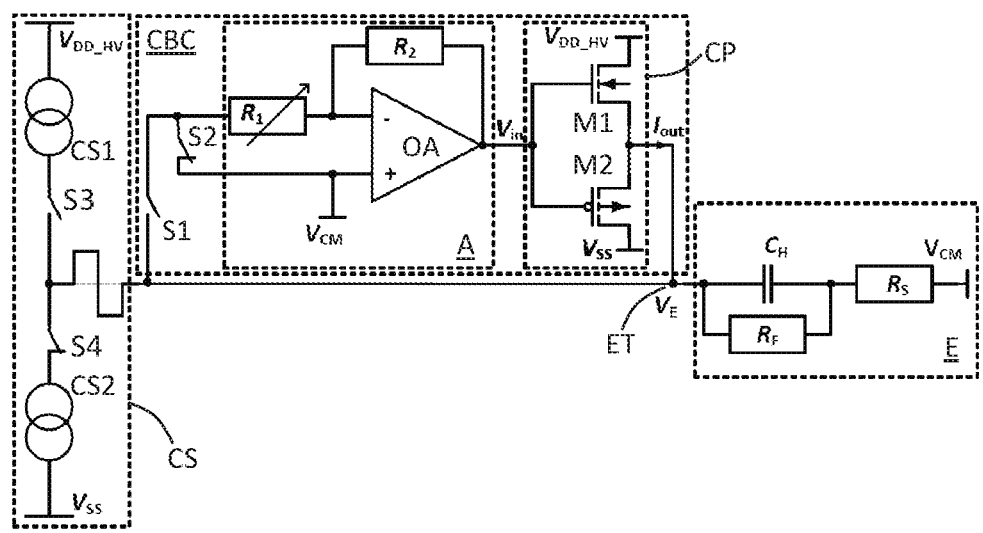
FIG. 2 shows an exemplary implementation of a stimulator circuit according to the improved concept.

FIG. 2 shows an exemplary implementation of a stimulator circuit according to the improved concept. The stimulator circuit comprises a charge balancing circuit CBC which is based on the implementation of the charge balancing circuit CBC of FIG. 1. The stimulator circuit further comprises a current source CS connected to the electrode terminal ET of the charge balancing circuit CBC and the electrode E also connected to the electrode terminal ET.

The amplifier A comprises an operational amplifier OA, a first resistive element R1 connected to a first input of the operational amplifier OA and connected to the electrode terminal ET via a first switch S1, and a second resistive element R2 connected between the first input of the operational amplifier OA and an output of the operational amplifier OA. The operational amplifier OA also comprises a second input which is connected to a reference terminal at which the reference voltage $V_{CM}$ is applied and coupled to the first input of the operational amplifier OA via the first resistive element R1 and a second switch S2.

In the shown example, the second resistive element R2 is for example implemented as a resistor and the first resistive element R1 is for example implemented as a tunable resistor. In alternative implementations, the second resistive element R2 may be implemented as a tunable resistor and/or the first resistive element R1 may be implemented as a non-tunable resistor.

The compensation stage CP is for example implemented as a push-pull stage, in particular a class B stage. The compensation stage CP comprises a first transistor M1 and a second transistor M2 being connected in series between a first supply terminal, at which a first supply voltage VDD_HV is applied, and a second supply terminal, at which a second supply voltage VSS is applied. The first transistor M1 may be implemented as a field effect transistor, in particular as a MOS field effect transistor, for example as an n-channel enhancement MOS transistor. The second transistor M2 is for example implemented complementary to the first transistor M1. The second transistor M2 may be implemented as a field effect transistor, in particular as a MOS field effect transistor, for example as a p-channel enhancement MOS transistor.

For example, the first supply voltage VDD_HV may be larger than the second supply voltage VSS. The reference voltage $V_{CM}$ may for example be chosen to approximately or exactly in the middle between the first and the second supply voltage VDD_HV, VSS. Said voltages are related to each other for example as $$V_{CM} \approx (VDD\_HV + VSS)/2, \quad (1)$$

wherein the first supply voltage VDD_HV is for example greater than the second supply voltage VSS.

The first and the second transistor M1, M2 are for example arranged in a common-drain configuration. That is, drain terminals of the first and the second transistor M1, M2 are for example connected to the first and the second supply terminal, respectively. Source terminals of the first and the second transistor M1, M2 are for example connected to each other. Furthermore, the electrode terminal ET is for example connected between the first and the second transistor M1, M2, for receiving the output current $I_{out}$. In particular, the electrode terminal ET is for example connected to the source terminals. Gate terminals of the first and the second transistor M1, M2 are for example connected to the output of the operational amplifier OA for receiving the intermediate voltage Vin.

The electrode E is for example implemented as a conventional electrode for functional electrical stimulation of biological tissue. It is therefore highlighted that the components shown in FIG. 2 with respect to the electrode E may not actually be comprised by the electrode E, but rather may represent an equivalent circuit for the electrode E being in contact with the biological tissue. In particular, the shown components may represent an equivalent circuit for an interface between the stimulator circuit and the biological tissue, which may comprise an electrolyte. The equivalent circuit of the electrode E comprises a Helmholtz capacitor CH and a solution-and-tissue resistor RS connected in series as well as a Faradaic resistor RF connected in parallel to the Helmholtz capacitor CH. The Helmholtz capacitor CH may represent a capacity of the interface between the stimulator circuit and the biological tissue. The solution-and-tissue resistor RS represents for example a combined resistance of the electrolyte and the tissue. The Faradaic resistor RF may for example represent reduction and oxidation currents taking place at the interface.

It is pointed out however, that the structure of the equivalent circuit is in no way obligatory for the improved concept or the stimulator circuit. In particular other equivalent circuits representing a corresponding electrode may be applicable.

The current source CS comprises a first internal current source CS1 connected to the first supply terminal for receiving the first supply voltage VDD_HV and a second internal current source CS2 connected to the second supply terminal for receiving the second supply voltage VSS. The first internal current source CS1 is further connected to the electrode terminal ET via a third switch S3 and the second internal current source CS2 is further connected to the electrode terminal via a fourth switch S4.

The switches S1, S2, S3, S4 may for example be controlled by a control unit (not shown in FIG. 2) that may be connected to the stimulator circuit and/or the charge balancing circuit CBC and/or the current source CS. The first and the second switch S1, S2 may be operated complementary to each other, that is, whenever the first switch S1 is opened the second switch S2 may be closed and vice versa.

The first switch S1 may for example be open and the second switch S2 may for example be closed during a pause mode of operation of the charge balancing circuit CBC, in particular during a time period when the current source CS supplies the current pulse to the electrode terminal ET. The resulting connection of the first and the second input of the operational amplifier OA may ensure that the intermediate voltage $V_{in}$ is zero or approximately zero during the pause mode. The first switch S1 may for example be closed and the second switch S2 may for example be opened during an operating mode of the charge balancing circuit CBC, in particular during a time period when no current pulse is supplied from the current source CS to the electrode terminal ET.

In alternative implementations, the first switch S1 may always be closed and the second switch S2 may always be open. In such implementations, the first and the second switch S1, S2 are optional. In such implementations, the charge balancing circuit CBC may also generate the output current $I_{out}$ during the current pulse being supplied by the current source CS. Then, amplitudes of the current pulse may be adapted accordingly to achieve a desired stimulation.

The third and the fourth switch S3, S4 may be operated complementary to each other during the pause mode, that is when the current source CS is supplying the current pulse to the electrode terminal ET. During the operation mode, the third and the fourth switch S3, S4 may be both open and/or the current source CS may be disconnected from the electrode terminal.

In the following it is assumed that the reference voltage $V_{CM}$ is equal to zero. Then it follows from relation (1) that, for positive VDD_HV, VDD_HV≈−VSS>0. However, another value for the reference voltage $V_{CM}$ is obviously possible and the following explanations are easily adapted by shifting the respective voltages by the value of the reference voltage $V_{CM}$.

Due to the shown connection of the operational amplifier OA and the resistive elements R1, R2, an amplification factor of the amplifier is equal to −r2/r1, wherein the effect of the inversion is already taken into account and r1 and r2 represent resistance values of the first and second resistive elements R1, R2, respectively. That is, the intermediate voltage $V_{in}$ and the electrode voltage $V_E$ are related to each other as $V_{in}=-V_E*r2/r1$.

The first and the second transistor M1, M2 feature respective first and second threshold voltages VTH1, VTH2. For example, absolute values of the first and the second threshold voltage VTH1, VTH2 may be equal to each other and to an absolute value of a threshold voltage VTH. Due to the depicted connection of the charge balancing circuit CBC, the intermediate voltage $V_{in}$ may for example be always smaller than or equal to the first supply voltage VDD_HV and larger than or equal to the second supply voltage VSS. Therefore, a gate-source voltage VGS of the first transistor and the second transistor M1, M2 may always be smaller or equal to a first drain-source voltage VDS1 of the first transistor M1. Consequently, the first drain-source voltage VDS1 may always be larger than a first overdrive voltage VOV1 of the first transistor M1, the first overdrive voltage given by the relation VOV1=VGS−VTH1. It follows that, whenever the gate-source voltage VGS is equal or larger than the first threshold voltage VTH1, the first transistor M1 may be operating in the saturation regime. The same holds analogously for the second transistor M2, resulting in that the second transistor M2 may always be operating in the saturation regime, whenever the gate-source voltage VGS of the second transistor M2 is smaller or equal than the second threshold voltage VTH2.

Consequently, assuming |VTH1|=|VTH2|=|VTH|, whenever the condition |VGS|≥|VTH| is fulfilled, an absolute value of the output current $I_{out}$ is given by the relation $$|I_{out}| \approx \beta * (|VGS| - |VTH|)^2 / 2, \quad (2)$$

Wherein β represents a transistor gain factor of the first and the second transistor M1, M2. The transistor gain factor β may for example depend on an aspect ratio of the gates of the first and the second transistor M1, M2. Further, the gate-source voltage VGS may be calculated according to the relation $$|VGS| = -|VE| * (1 + r2/r1). \quad (3)$$

By this arrangement, the output current $I_{out}$ is generated in such a way that the electrode voltage $V_E$ is driven back towards and/or into the safety range, whenever the electrode voltage $V_E$ lies outside of the safety range. To this end, the resistance value r2, and thereby the amplification factor −r2/r1, may be tuned such that the gate-source voltage VGS is equal to the first threshold voltage VTH1 if the electrode voltage $V_E$ is equal or approximately equal to a lower boundary of the safety range. Then, for |VTH1|=|VTH2|=|VTH|, the gate-source voltage VGS is equal to the second threshold voltage VTH2 if the electrode voltage $V_E$ is equal or approximately equal to an upper boundary of the safety range. In other words, the upper and the lower boundary of the safety range follow from equation (3) by inserting VTH for VGS and solving the equation for $V_E$. This results in the values ±|VTH|/(1+r2/r1) for the upper and the lower boundary of the safety range, respectively.

To make this more transparent, we provide a simple numerical example in the following. It is assumed that the safety range is given by a voltage interval from −100 mV to 100 mV. Furthermore, it is assumed that the first and second threshold voltage are given by VTH1=6V and VTH2=−6V, respectively. Consequently, the second resistive element R2 may be tuned to achieve the amplification factor −r2/r1=−59, resulting in |VGS|=6V for |VE|=100 mV according to equation (3).

It is further assumed that the current source CS has supplied a current pulse to the electrode E and after the current pulse, an electrode voltage $V_E$ of $V_E$=−200 mV remains at the electrode E and at the electrode terminal ET, respectively. This may for example occur if the current pulse is an unbalanced biphasic current pulse. It is further assumed that the first switch S1 was open during the current pulse and is closed after the current pulse, while the second switch S2 was closed during the current pulse and is opened after the current pulse. Then, the amplifier A inverts and amplifies the electrode voltage $V_E$ to generate an intermediate voltage $V_{in}$ of $V_{in}$=11.8V and a resulting gate-source voltage of VGS=12V. Consequently, the first transistor M1 is conducting, while the second transistor M2 is not conducting.

Therefore, the output current $I_{out}$ is positive, that is the direction of the output current $I_{out}$ is from the first supply terminal to the electrode terminal $V_E$ and its absolute value is given by equation (2). As a consequence, the absolute value of the electrode voltage $V_E$ is reduced until the electrode voltage $V_E$ reaches the lower boundary of the safety range, that is $V_E$=−100 mV. In this case the gate-source voltage VGS becomes equal to VTH1, namely 6V. Therefore first transistor M1 becomes non-conducting and the output current $I_{out}$ drops to zero.

Figure 3:
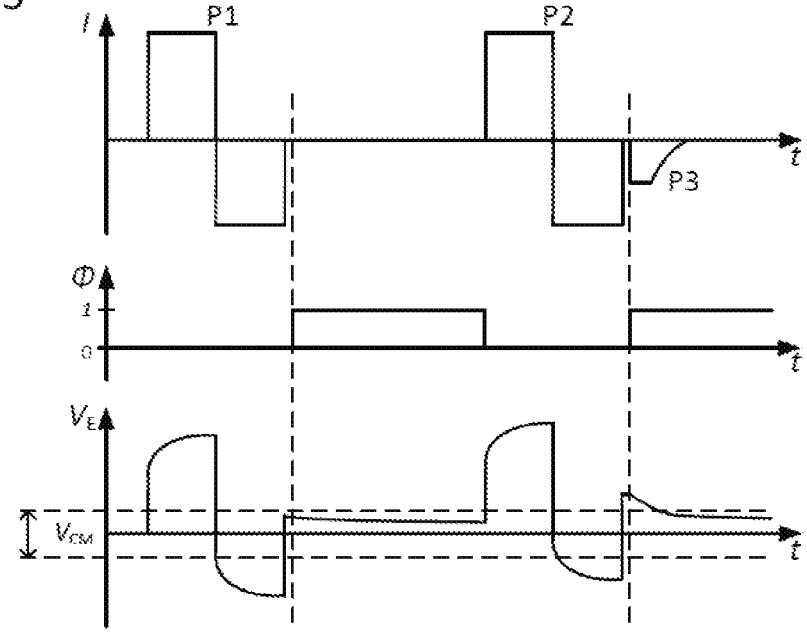
FIG. 3 shows schematic diagrams of a current and an electrode voltage as a function of time in exemplary implementations of charge balancing circuits and/or stimulator circuits according to the improved concept.

FIG. 3 shows schematic diagrams of a current I and an electrode voltage $V_E$ as a function of time t in exemplary implementations of charge balancing circuits CBC and/or stimulator circuits according to the improved concept. The current I may for example represent a current pulse being supplied from the current source CS to the electrode E as well as the output current $I_{out}$ for example in an implementation of the stimulator circuit according to FIG. 2.

Furthermore, a switch signal Φ controlling and the first and second switch S1, S2 is shown. Therein, the first switch S1 is opened and the second switch S2 is closed whenever the switch signal Φ is equal to zero. The first switch S1 is closed and the second switch S2 is opened whenever the switch signal Φ is equal to one.

A first current pulse P1 is supplied from the current source CS to the electrode terminal ET. Therein, the first current pulse P1 consists of a first part featuring a positive value of the current and of a second part featuring a negative value of the current. During a time period of the first part of the first current pulse P1 the electrode voltage $V_E$ is for example larger than the reference voltage $V_{CM}$ and increasing, while during a time period of the second part of the first current pulse P1 the electrode voltage $V_E$ is for example smaller than the reference voltage $V_{CM}$ and decreasing.

In the shown example, the first part of the first current pulse P1 has a slightly larger amplitude than the second part of the first current pulse P1, that is the first current pulse is an unbalanced biphasic current pulse. Consequently, the electrode voltage $V_E$ does not drop to the reference voltage $V_{CM}$ at the end of the first current pulse P1 but assumes a value larger than the reference voltage $V_{CM}$. However, the electrode voltage $V_E$ remaining at the end of the first current pulse P1 lies within the safety range indicated by horizontal dashed lines. Consequently, according to explanations with respect to FIGS. 1 and 2 the charge balancing circuit CBC does not generate an output current $I_{out}$.

A second current pulse P2 is supplied from the current source CS to the electrode terminal ET a certain time after the first current pulse P1 has ended. Therein, the second current pulse P2 consists of a first part featuring a positive value of the current and of a second part featuring a negative value of the current. During a time period of the first part of the first current pulse P2 the electrode voltage $V_E$ is for example larger than the reference voltage $V_{CM}$ and increasing, while during a time period of the second part of the second current pulse P2 the electrode voltage $V_E$ is for example smaller than the reference voltage $V_{CM}$ and decreasing.

In the shown example, the first part of the second current pulse P2 has a slightly larger amplitude than the second part of the second current pulse P2, that is the second current pulse is an unbalanced biphasic current pulse. Therefore, and due to a remaining electrode voltage $V_E$ resulting from the first current pulse P1, the electrode voltage $V_E$ lies outside the safety range after the second current pulse P2. Consequently, the charge balancing circuit CBC, in particular the compensation stage CP, generates the output current $I_{out}$ according to the explanations with respect to FIGS. 1 and 2 to drive the electrode voltage $V_E$ towards and/or into the safety range. The respective output current $I_{out}$ generated by the charge balancing circuit CBC is indicated by a third current pulse P3.

Figure 4:
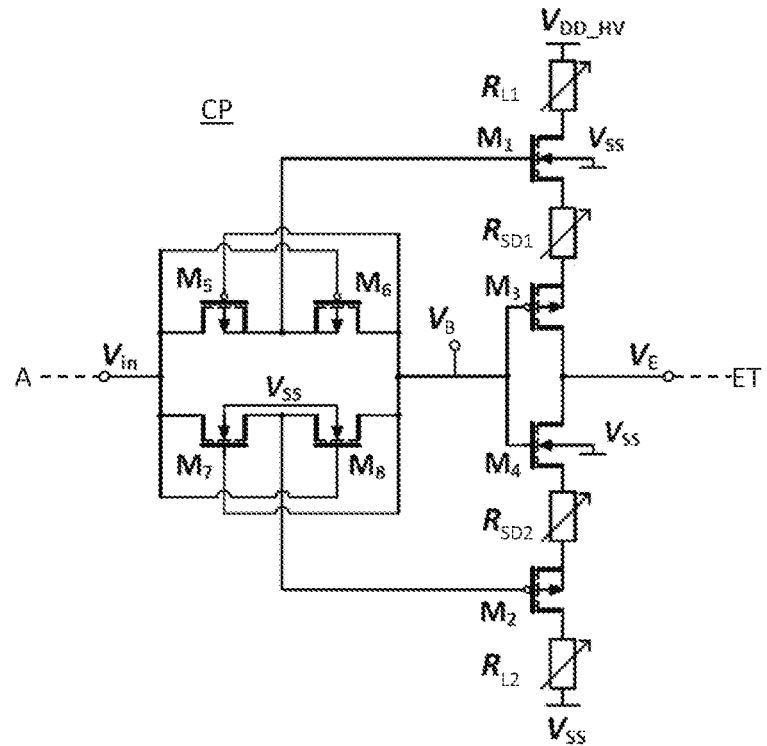
FIG. 4 shows an exemplary implementation of a compensation stage for being used in an implementation of a charge balancing circuit and/or a stimulator circuit according to the improved concept.

FIG. 4 shows an exemplary implementation of a compensation stage CP for being used in an implementation of a charge balancing circuit CBC and/or a stimulator circuit according to the improved concept. The compensation stage CP may for example be used in a charge balancing circuit CBC and/or a stimulator circuit according to one of FIGS. 1 and 2. In particular, the compensation stage CP of FIG. 4 is based on the compensation stage CP described with respect to FIG. 2. As indicated by dashed lines, the compensation stage CP is for example connected between the amplifier A and the electrode terminal ET.

In addition to the implementation of FIG. 2, the compensation stage CP of FIG. 4 comprises a first current limiting component RL1 coupled between the first supply terminal and the first transistor M1 and a second current limiting component RL2 coupled between the second supply terminal and the second transistor M2. The compensation stage CP also comprises a first further current limiting component RSD1 coupled between the first transistor M1 and the electrode terminal ET and a second further current limiting component RSD2 coupled between the second transistor M2 and the electrode terminal ET.

Furthermore, the compensation stage CP comprises a third transistor M3 connected between the first transistor M1 and the electrode terminal ET, in particular between the first further current limiting component RSD1 and the electrode terminal ET. The compensation stage CP further comprises a fourth transistor M4 coupled between the second transistor and the electrode terminal ET, in particular between the second further current limiting component RSD2 and the electrode terminal ET. Control terminals of the third and fourth transistor M3, M4 are connected to a bias voltage $V_B$.

The compensation stage CP also comprises a first and a second protection transistor M5, M6 connected in series as well as a third and a fourth protection transistor M7, M8 connected in series. Therein, the first and the third protection transistor M5, M7 are connected to the intermediate voltage $V_{in}$, while the second and the fourth protection transistor M6, M8 are connected to the bias voltage $V_B$. Control terminals of the first and the third protection transistor M5, M7 are connected to the bias voltage $V_B$, while control terminals of the second and fourth protection transistor M6, M8 are connected to the intermediate voltage Vin.

The third and the fourth transistor M3, M4 are for example implemented as field effect transistors, for example as MOS field effect transistors. The third transistor M3 is for example implemented as p-channel enhancement MOS field effect transistor, while the fourth transistor M4 is for example implemented as an n-channel enhancement MOS field effect transistor. A source terminal of the third transistor M3 may for example be coupled to the source terminal of the first transistor M1 and a drain terminal of the third transistor M3 may for example be coupled to the electrode terminal ET, or vice versa. A source terminal of the fourth transistor M4 may for example be coupled to the source terminal of the second transistor M2 and a drain terminal of the fourth transistor M4 may for example be coupled to the electrode terminal ET.

In the example of FIG. 4, a bulk terminal of the first transistor M1 is connected to the second supply terminal, while a bulk terminal of the second transistor M2 is for example connected to the source terminal of the second transistor M2. Such a connection is, however, not mandatory and may for example be determined by a production technology of the first and the second transistor M1, M2. For example the bulk terminal of the first transistor M1 may be connected to the source terminal of the first transistor M1, to a potential being lower than the source potential of the first transistor M1 or to the second supply terminal. For example the bulk terminal of the second transistor M2 may be connected to the source terminal of the second transistor M2, to a potential being higher than the source potential of the second transistor M2 or to the first supply terminal. In particular, the bulk terminals of the first and the second transistor M1, M2 may be connected asymmetrically as depicted or symmetrically.

In the example of FIG. 4, a bulk terminal of the third transistor M3 is connected to the source terminal of the third transistor M3, while a bulk terminal of the fourth transistor is connected to the second supply terminal. This means, the bulk terminal of the third transistor M3 is connected in analogy to the connection of the bulk terminal of the second transistor M2, while the bulk terminal of the fourth transistor M3 is connected in analogy to the connection of the bulk terminal of the first transistor M1.

The asymmetrical connection of the bulk terminals of the first and the second transistor M1, M2 as shown in FIG. 4 may for example cause different absolute values of the first and the second threshold voltage VTH1, VTH2. The asymmetric connection of the bulk terminals of the third and the fourth transistor M3, M4 as shown in FIG. 4 may for example compensate the asymmetry of the first and the second transistor M1, M2 and result in identical or approximately identical absolute values of effective threshold voltages for the first and second transistor M1, M2. To this end, the bias voltage $V_B$ may be adjusted correspondingly. For example, the bias voltage $V_B$ may be adjusted according to the equation $$V_B = V_{CM} - (|VTH1| + |VTH3| - |VTH2| - |VTH4|)/2, \qquad (4)$$

with the third threshold voltage VTH3 and the fourth threshold voltage VTH4 being threshold voltages of the third and the fourth transistor M3, M4, respectively.

In addition to the described effect of compensating the asymmetric bulk connection, the third and the fourth transistor M3, M4 may lead to a shielding effect, that is the first and the second transistor M1, M2 may be controlled independently of the electrode voltage VE.

The first and the second protection transistor M5, M6 are for example implemented as field effect transistors, in particular as MOS field effect transistors, for example as p-channel enhancement MOS transistors. The third and the fourth protection transistor M7, M8 are for example implemented as field effect transistors, in particular as MOS field effect transistors, for example as n-channel enhancement MOS transistors. In the shown example, a bulk terminal of the first protection transistor M5 is for example connected to the source terminal of the first protection transistor M5 and a bulk terminal of the second protection transistor M6 is for example connected to the source terminal of the second protection transistor M6. Bulk terminals of the third and fourth protection transistor M7, M8 are for example connected to the second supply terminal. However, as pointed out for the first and the second transistor M1, M2, this specific bulk connection is not mandatory.

By the arrangement of the first and the second protection transistor M5, M6 it may for example be achieved that the first protection transistor M5 is conductive if the intermediate voltage $V_{in}$ is larger than the bias voltage $V_B$ and is non-conductive in the opposite case. Analogously, the second protection transistor M6 may for example be conductive if the bias voltage $V_B$ is larger than the intermediate voltage $V_{in}$ and non-conductive in the opposite case. In this way, it may for example be achieved that a voltage applied at the gate terminal of the first transistor M1 is limited by the bias voltage $V_B$. In particular, a gate-drain voltage of the first transistor M1 may be limited by the bias voltage $V_B$.

By the arrangement of the third and the fourth protection transistor M7, M8 it may for example be achieved that the second protection transistor M7 is conductive if the intermediate voltage $V_{in}$ is smaller than the bias voltage $V_B$ and is non-conductive in the opposite case. Analogously, the third protection transistor M8 may for example be conductive if the bias voltage VB is smaller than the intermediate voltage $V_{in}$ and non-conductive in the opposite case. In this way, it may for example be achieved that a voltage applied at the gate terminal of the second transistor M2 is limited by the bias voltage $V_B$. In particular, a gate-drain voltage of the second transistor M2 may be limited by the bias voltage $V_B$.

The first and the second current limiting component RL1, RL2 and/or the first and the second further current limiting component RSD1, RSD2 may for example be implemented as resistors, in particular as tunable resistors, for example as digitally tunable resistors.

By means of the first and the second current limiting component RL1, RL2, the output current $I_{out}$ may for example be limited. For example, drain potentials of the first and the second transistor M1, M2 may be reduced. Consequently, it may be achieved that the first and/or the second transistor M1, M2 do not operate in a saturation regime. In particular, the first and/or the second transistor M1, M2 may be forced to stay in linear regime of operation by causing pinch off. Thereby, the output current $I_{out}$ may be effectively limited to a maximum output current.

By means of the first and the second further current limiting component RSD1, RSD2, the output current $I_{out}$ may for example be limited. For example, source potentials of the first and the second transistor M1, M2 may be reduced. Consequently, the slope of the output current is changed, thereby, source degeneration may be used to limit the output current $I_{out}$ effectively to a maximum output current.

Figure 5:
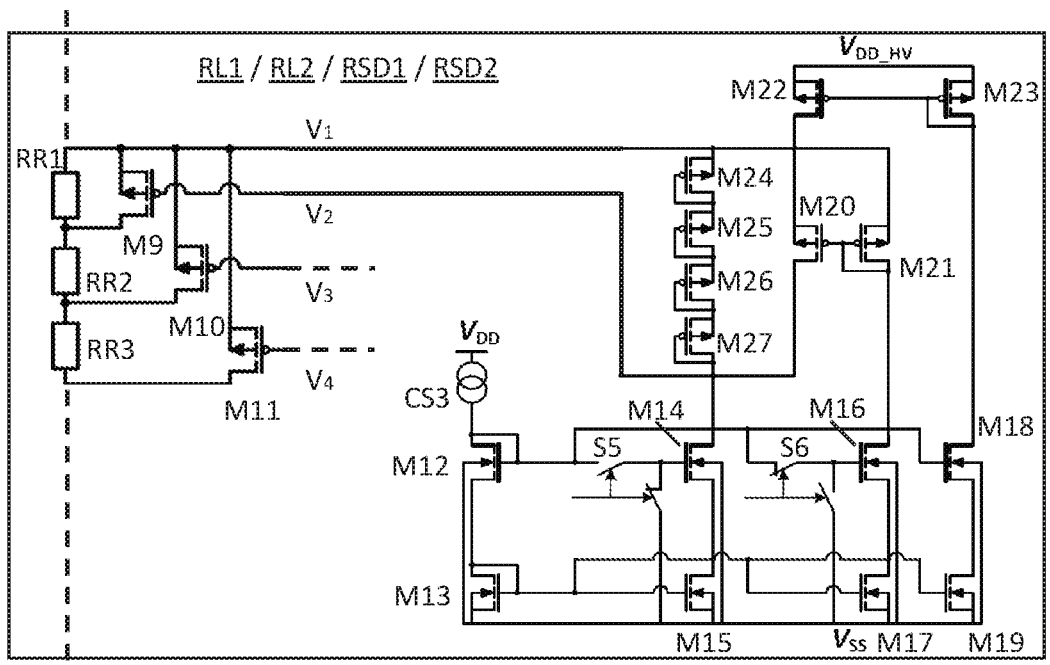
FIG. 5 shows an exemplary implementation of a current limiting component or a further current limiting component for being used in an implementation of a charge balancing circuit and/or a stimulator circuit according to the improved concept.

The current limiting components RL1, RL2 and the further current limiting components RSD1, RSD2 may be implemented for example as conventional digitally tunable resistors. An exemplary implementation of such digitally tunable resistor is shown in FIG. 5.

In alternative implementations, at least one of the current limiting components RL1, RL2 and the further current limiting components RSD1, RSD2 is implemented as a transistor. Then, a resistance of the respective component RL1, RL2, RSD1, RSD2 may be determined by an aspect ratio of a gate of the transistor. In further implementations, at least one of the current limiting components RL1, RL2 and the further current limiting components RSD1, RSD2 is implemented as several transistors coupled in parallel that may be selectively switched conducting or non-conducting in order to determine a respective resistance.

In alternative implementations, the compensation circuit CP does not comprise the protection transistors M5, M6, M7, M8, the third and fourth transistors M3, M4, the current limiting components RL1, RL2 and/or the further current limiting components RSD1, RSD2. In particular, said components may or may not be comprised by the compensation circuit CP in all possible combinations.

Figure 6:
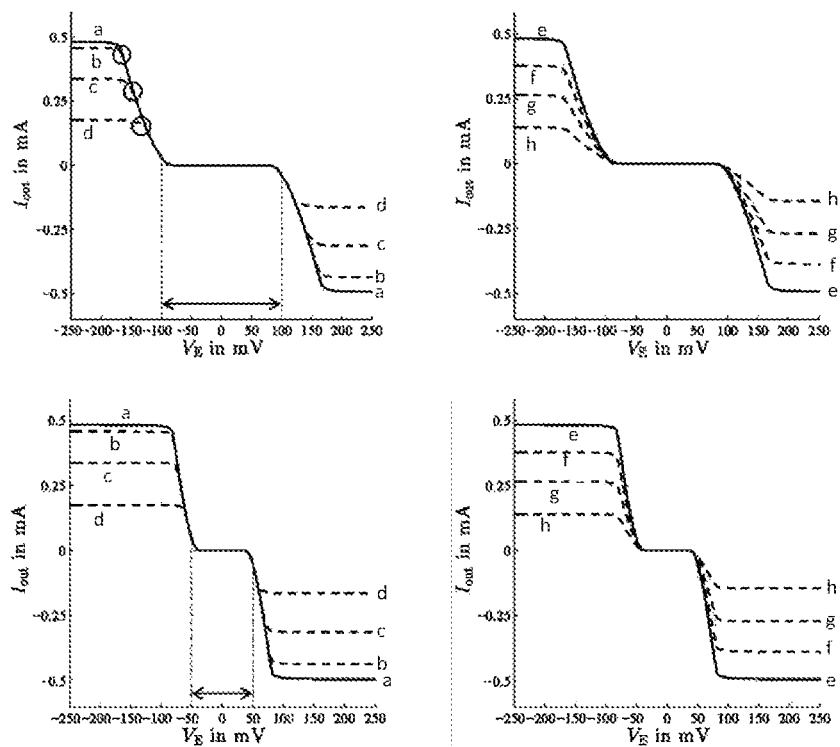
FIG. 6 shows schematic diagrams of an output current as a function of an electrode voltage in exemplary implementations of charge balancing circuits and/or stimulator circuits according to the improved concept.

FIG. 6 shows schematic diagrams of an output current $I_{out}$ as a function of an electrode voltage $V_E$ in exemplary implementations of charge balancing circuits CBC and/or stimulator circuits according to the improved concept. In particular, the output currents $I_{out}$ shown in FIG. 6 may occur in implementations according to FIG. 4.

In the upper left panel of FIG. 6, the output current $I_{out}$ is shown as a function of the electrode voltage $V_E$ for a current limitation achieved by means of the first and/or the second current limiting component RL1, RL2. In particular, resistances of the first and the second further current limiting component RSD1, RSD2 are zero in this case.

The shown curves a, b, c, d correspond to different resistance values of the first and/or the second current limiting component RL1, RL2, wherein said resistance values are increasing in the order a, b, c, d. In particular, the resistance value of the first and/or the second current limiting component RL1, RL2 may be zero for curve a.

The curves shown in the lower left panel of FIG. 6 correspond to the curves shown in the upper left panel of FIG. 6. However, the safety range is different, namely from approximately −100 mV to approximately 100 mV in the upper left panel and from approximately −50 mV to approximately 50 mV in the lower left panel, achieved by means of the amplification factor −r1/r2.

The current limitation due to the first and/or the second current limiting component RL1, RL2 results in the particular shapes of the curves a, b, c, d. In particular, the various resistance values of the current limiting component RL1, RL2 leave the slopes of the output current $I_{out}$ basically unchanged, while the dynamic range becomes smaller with increasing resistance values.

In the upper right panel of FIG. 6, the output current $I_{out}$ is shown as a function of the electrode voltage $V_E$ for a current limitation achieved by means of the first and/or the second further current limiting component RSD1, RSD2. In particular, resistances of the first and the second current limiting component RL1, RL2 are zero in this case.

The shown curves e, f, g, h correspond to different resistance values of the first and/or the second further current limiting component RSD1, RSD2, wherein said resistance values are increasing in the order e, f, g, h. In particular, the resistance value of the first and/or the second further current limiting component RSD1, RSD2 may be zero for curve e.

The curves shown in the lower right panel of FIG. 6 correspond to the curves shown in the upper right panel of FIG. 6. However, the safety range is different, namely from approximately −100 mV to approximately 100 mV in the upper left panel and from approximately −50 mV to approximately 50 mV in the lower left panel, achieved by means of the amplification factor −r1/r2.

The current limitation due to the first and/or the second further current limiting component RSD1, RSD2 results the particular shapes of the curves e, f, g, h. In particular, the various resistance values of the current limiting component RSD1, RSD2 leave dynamic range of the output current $I_{out}$ basically unchanged, while the slope of the curves becomes smaller with increasing resistance values.

It is pointed out, that a current limitation may also be achieved by the first and/or second current limiting components RL1, RL2 and by the first and/or second further current limiting components RSD1, RSD2 at the same time. The shape of the resulting curves for the output current $I_{out}$ can be understood as corresponding mixtures of shapes shown in the left and right panels of FIG. 6, respectively.

Figure 7:
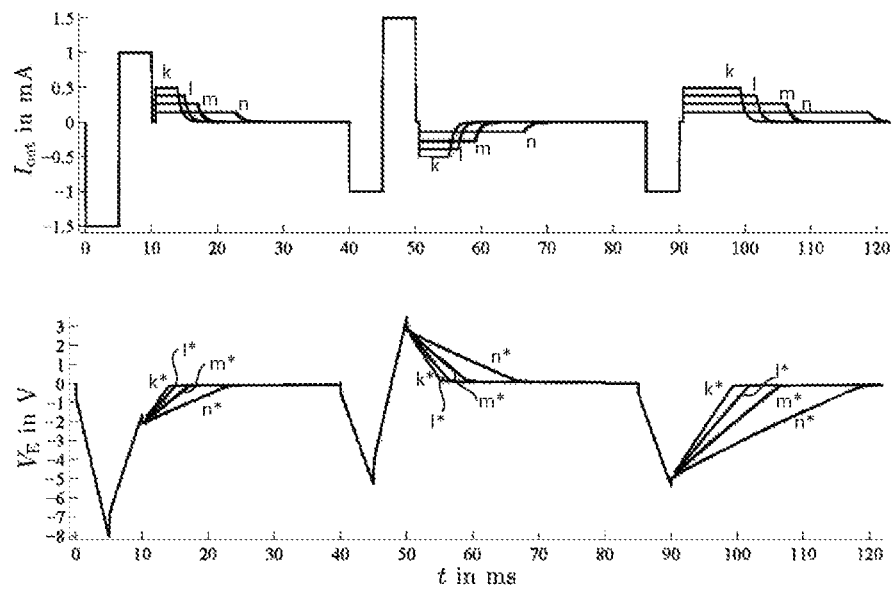
FIG. 7 shows schematic diagrams of output currents and electrode voltages as a function of time in exemplary implementations of charge balancing circuits and/or stimulator circuits according to the improved concept.

FIG. 7 shows schematic diagrams of output currents $I_{out}$ and electrode voltages $V_E$ as a function of time t in exemplary implementations of charge balancing circuits CBC and/or stimulator circuits according to the improved concept. In particular, the output currents $I_{out}$ and electrode voltages $V_E$ shown in FIG. 7 may occur in implementations according to FIG. 4.

The upper panel of FIG. 7 shows the output current $I_{out}$ as a function of time t for different values of the maximum output current realized by means of the current limiting components RL1, RL2 and/or the further current limiting component RSD1, RSD2.

During a time from approximately 0 ms to approximately 10 ms, a biphasic current pulse is supplied from the current source CS, which is reflected in a biphasic rectangular signal in the curves of $I_{out}$. During this time, the charge balancing circuit CBC is for example disconnected from the electrode terminal ET. Then, between approximately 10 ms and approximately 40 ms, the charge balancing circuit CBC is connected to the electrode terminal ET and the output current $I_{out}$ is generated by the charge balancing circuit CBC according to the explanations above for the preceding Figures. Therein, the shown curves k, l, m, n correspond to different values of the maximum output current. In particular, the value of the maximum output current decreases in the order k, l, m, n, resulting in an increasing width and a decreasing maximum amplitude of the curves k, l, m, n.

Analogously, between approximately 40 ms and approximately 50 ms, another biphasic current pulse is supplied from the current source CS. During this time, the charge balancing circuit is for example again disconnected from the electrode terminal. Then, between approximately 50 ms and approximately 85 ms, the charge balancing circuit CBC is connected to the electrode terminal ET and the output current $I_{out}$ is generated by the charge balancing circuit CBC as explained above. The curves k, l, m, n correspond to the different values of the maximum output current as explained above.

Between approximately 85 ms and approximately 90 ms, a monophasic current pulse is supplied from the current source CS. During this time, the charge balancing circuit CBC is for example again disconnected from the electrode terminal. Then, after approximately 90 ms, the charge balancing circuit CBC is connected to the electrode terminal ET and the output current $I_{out}$ is generated by the charge balancing circuit CBC as explained above. The curves k, l, m, n correspond to different values of the maximum output current as explained above.

The lower panel of FIG. 7 shows the electrode voltage $V_E$ as a function of time t for different values of the maximum output current realized by means of the current limiting components RL1, RL2 and/or the further current limiting component RSD1, RSD2. Therein the curves k*, l*, m*, n* correspond to the values of the maximum output currents of the curves k, l, m, n of the upper panel, respectively.

From the curves shown in FIG. 7, it can be seen that the improved concept may be used for charge balancing for functional electric stimulation using monophasic or biphasic current pulses.

By means of the improved concept, power consumption of charge balancing for functional electrical stimulation of biological tissue may be decreased. In particular, the described compensation stage CP may be essentially inactive when the electrode voltage $V_E$ lies within the safety range. On the other hand, the described architectures for the compensation stage CP allow for an improved response time once the electrode voltage $V_E$ lies outside the safety range.

Further, the improved concept also allows for a reduced space being required. This is in particular achieved since the compensation stage does not need any external means to define the safety range, the voltage window or an operating range. This result from the possibility to use the first and second supply voltages VDD_HD, VSS also being used for generating the current pulse by the current source CS.

FIG. 8 shows a further exemplary implementation of a stimulator circuit according to the improved concept. For example, a conceptual configuration of a current-controlled stimulation setup and proposed charge balancing circuit is exemplarily shown for a monopolar configuration in FIG. 8. The electrical equivalent model of the electrode-electrolyte tissue interface is represented by the Helmholtz double-layer capacitor $C_H$, the solution and tissue resistance $R_S$, and the Faradaic resistance $R_F$, which models reduction and oxidation currents.

As discussed previously, monophasic stimulation consists of a cathodic pulse $I_{Stim}$, which depolarizes the nerve and evokes the desired physiological effect, whereas biphasic stimulation uses an additional anodic counter pulse of opposite sign, reversing the electrochemical reactions. However, due to process variations the charge of the cathodic stimulus might not be fully retracted during the anodic phase. Resulting excess charge across the tissue interface may cause irreversible Faradaic reactions that will lead to electrode and tissue destruction. To avoid this, the electrode potential $V_E$ with respect to $V_{CM}$ must be controlled and kept below its critical values, i.e. the safety limit. Once $V_E$ exceeds the safety limits, a compensation current $I_{CB}$ is applied, corresponding to the output current $I_{out}$.

In the present embodiment of FIG. 8, the charge balancer is formed of a fully differential operational transconductance amplifier (FDOTA) A as high voltage (HV) monitoring unit and a current driver stage CP for charge compensation, shown in a simplified form in FIG. 8.

During operation, for example, directly after each stimulus $S_{CB}=\overline{S_c \cup S_a}$ turns high. The FDOTA starts monitoring $V_E$ and steers the current driver to balance the remaining charges instantaneously. The charge balancer becomes autonomously inactive, once $V_E$ has reached the safety limits. However, $S_{CB}$ stays high until the next stimulus begins, thus, being able to react to disturbances. In contrast to conventional approaches that are limited to a fixed supply of e.g. 22V due to technological limits, the improved concept overcomes these limitations by its circuit design using for example a configurable quad-rail architecture.

FIG. 9 shows a representation of an adaptive quad-rail system, wherein FIG. 9A shows the quad-rail system at a minimum possible supply range, FIG. 9B at a medium possible supply range and FIG. 9C at a maximum possible supply range. The quad-rail system is the basis of the design methodology, consisting of four supply rails, as depicted in FIG. 9. The supplies $V_{DD\_LV}$ and $V_{SS\_LV}$, as well as $V_{DD\_HV}$ and $V_{SS\_HV}$, which may be provided externally, form low voltage (LV) domains, denoted as $\Delta V_{LV}$, each fixed to 3.3 V. However, the supply rails $V_{DD\_HV}$ and $V_{SS\_HV}$ lie within an HV environment $\Sigma V_{HV}$. The voltage range of the outer supply rails $V_{DD\_HV}$ and $V_{SS\_LV}$ is supposed to be adapted to the supply of various stimulators. It has been shown by measurements that the voltage range between the outer supply rails $V_{DD\_HV}$ and $V_{SS\_LV}$ can be varied from 6.6 to 38 V in total without changing the systems characteristic and efficacy. The two $\Delta V_{LV}$ domains contain and protect the active electronics independent of the HV environment. All transistors in the upper $\Delta V_{LV}$ domain are of isolated substrate type, since they are exposed to high bulk-substrate voltages. Designing the system in accordance to this quadrail methodology even allows for an asymmetric supply range displacement with respect to the body's quiescent potential $V_{CM}$. The supply range displacement may improve the system efficiency in example for monophasic stimulation, where the voltage between $V_{SS}$ and $V_{CM}$ may be needed at the maximum of 19 V to provide high stimulus currents, whereas the $V_{DD\_HV}$ supply may be sufficiently high with 3.3 V above $V_{CM}$ to fully compensate remaining charges with small $I_{CB}$ amplitudes.

Figure 10:
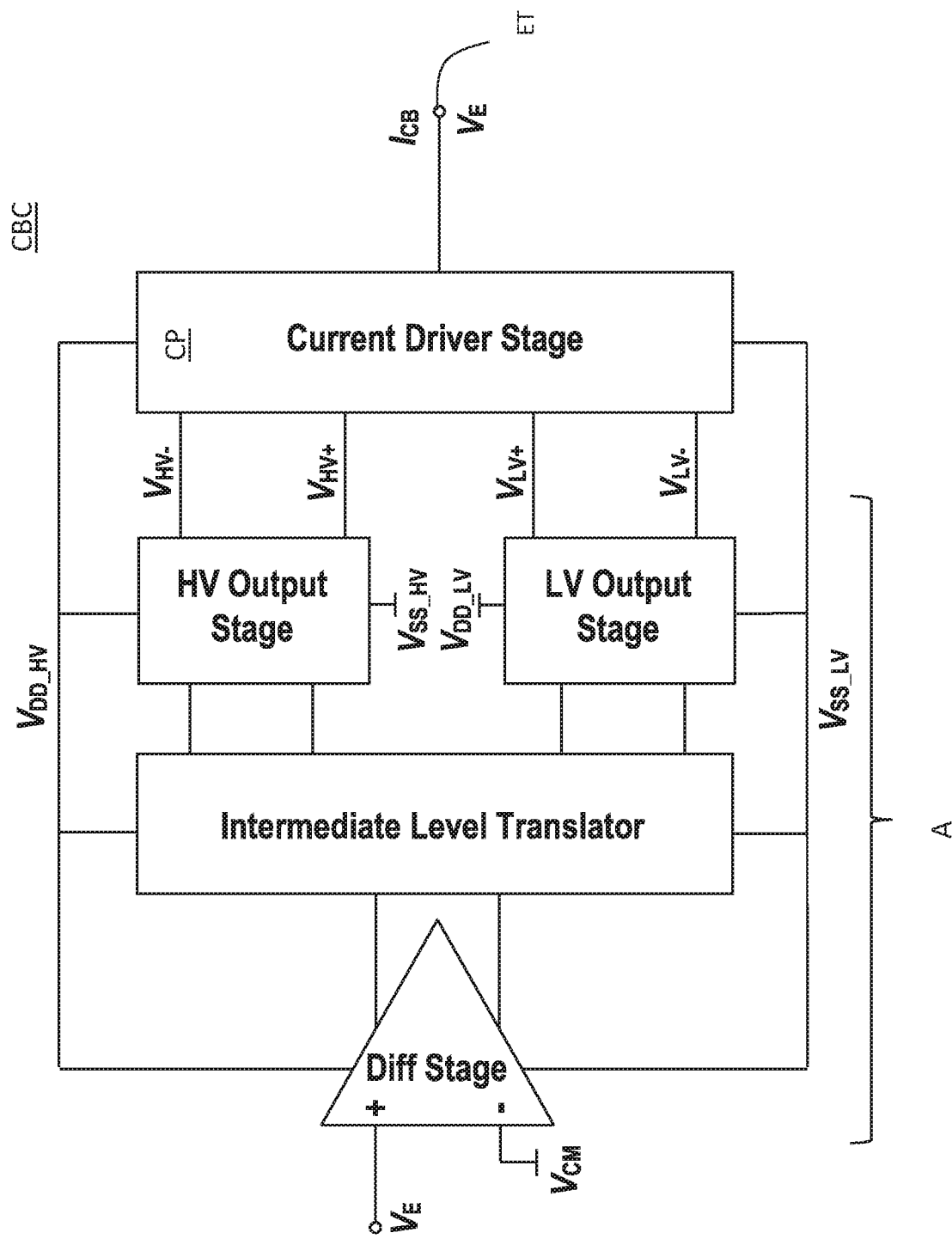
FIG. 10 shows an exemplary implementation of a charge balancing circuit according to the improved concept.

FIG. 10 shows an exemplary implementation of a charge balancing circuit CBC according to the improved concept on a high level basis. The charge balancing circuit comprises an FDOTA formed of four blocks: the differential input stage, an intermediate level translator (ILT), and the LV and HV output stages. The FDOTA compares $V_E$ to $V_{CM}$ and enhances the differential input voltage by its open loop gain. Its differential output signals $V_{HV+}$, $V_{HV-}$ and $V_{LV+}$, $V_{LV-}$ are shifted into the two $\Delta V_{LV}$ quad-rail domains to steer the current driver CP. The required low gain, in the range of 20 to 50, is realized by an open loop configuration of the FDOTA. An advantage over an external feedback is its high input impedance, i.e. a DC decoupling between the FDOTA as charge sensor and the tissue interface.

Figure 11:
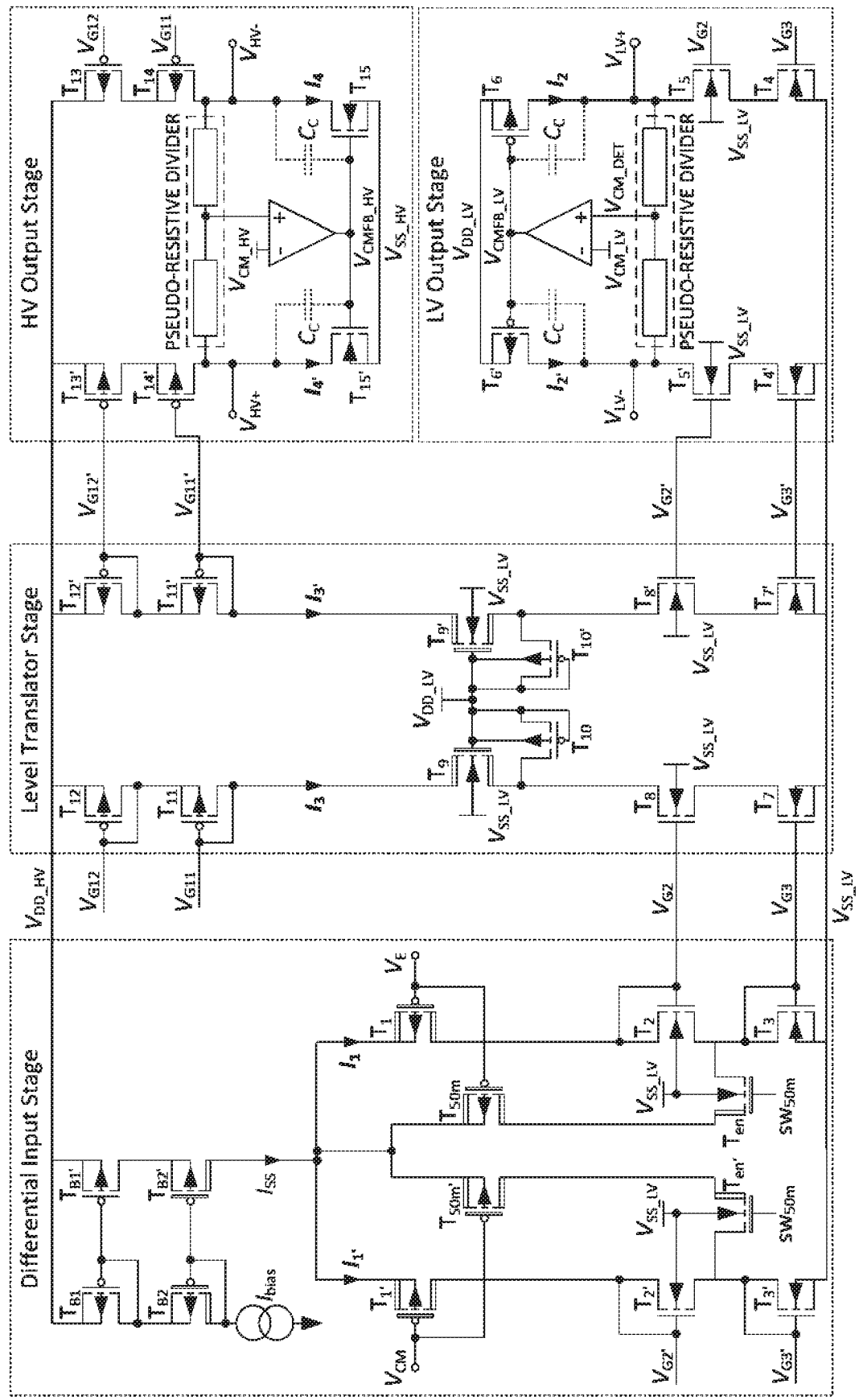
FIG. 11 shows an exemplary implementation of a fully differential operational transconductance amplifier for a charge balancing circuit according to the improved concept.

FIG. 11 shows an exemplary implementation of a FDOTA for a charge balancing circuit according to the improved concept on a transistor level basis. The HV transistors $T_{1,1'}$ represent the basic input pair of the differential input stage, where $V_E$ and $V_{CM}$ are applied. The FDOTA allows switching between the two safety limit values by changing the input transconductance gmin of the differential input stage, and thus, the FDOTA's open loop gain. Therefore, two additional input transistors $T_{50m,50m'}$ are introduced in parallel to T1,1', increasing gmin. The input gain of around 23.8 for ±100 mV is increased to around 47.6 for ±50 mV safety limit. The switching transistors $T_{en,en'}$ are connected to the sources of $T_{2,2'}$ instead of their drains to lower the source voltage of $T_{en,en'}$, and thus, ensure that a signal sw50m of 3.3 V activates the switch. The differential input signal is directly mirrored by $T_{3,3'}$ and $T_{2,2'}$ to $T_{4,4'}$ and $T_{5,5'}$ into the LV output stage, which operates in the lower $\Delta V_{LV}$ subrange. However, the translation of the differential input signal into the upper $\Delta V_{LV}$ subrange necessitates a level shift. The differential current is therefore mirrored into the ILT stage by $T_{2,2'}$, $T_{3,3'}$ and $T_{7,7'}$, $T_{8,8'}$. The ILT stage operates in the overall HV environment. Hence, the drains of $T_{8,8'}$ should be protected from HV. For that purpose, two HV transistors $T_{9,9'}$ with their gates fixed to $V_{DD\_LV}$ are introduced. In saturation, their gate-source voltages prevent the drains of $T_{8,8'}$ to exceed $V_{DD\_LV}$. However, in a zero current condition of $I_3$ or $I_{3'}$ the drain of $T_8$ or $T_{8'}$ is exposed to a high ohmic node, and an additional protection scheme is necessary: two diode-connected PMOS transistors $T_{10,10'}$ are placed between the sources and gates of $T_{9,9'}$, clamping the drain of $T_{8,8'}$ to a maximum of $V_{DD\_LV}$. The LV and HV output stages are designed symmetrically. Due to the low open loop gain requirement of the FDOTA, the load transistors $T_{6,6'}$, $T_{15,15'}$ are biased in triode region to decrease the output resistance. Their gates are biased by a common mode feedback (CMFB) circuit, controlling the output common mode to half the $\Delta V_{LV}$ range.

The proposed CB implementation makes use of the full output swing of the FDOTA of 3.3 V to fully activate the current driver. Therefore, as an example, a resistive voltage divider is used to detect the actual common mode voltage $V_{CM\_DET}$. $V_{CM\_DET}$ is then compared to the wanted common mode voltage $V_{CM\_LV}$ and increased by the positive gain of a single-stage differential amplifier, as shown in FIG. 11. The HV CMFB design is analogous to the LV one, however, with an inverted architecture and with isolated transistor types due to the increased bulk-substrate requirement of the HV output stage. Other implementations for detecting the actual common mode voltage $V_{CM\_DET}$ are still possible, e.g. with other kinds of voltage dividers.

The CMFB amplifier together with the output stage of the FDOTA represents a two-stage amplifier. For stability reasons the dominant pole that originates from the CMFB amplifier, is further separated by using Miller compensation. Therefore, the capacitances $C_C$ of 800 fF are introduced between the gate and the drains of the load transistor of the FDOTA T6,6o, as shown in FIG. 11. A second pole arises at the output of the FDOTA, where the pseudo-resistor is connected, and is compensated by inducing a zero via the capacitors $C_Z$ of 400 fF. A third pole appears at the input of the CMFB amplifier. The phase margin of LV and HV CMFB loops are optimized to 51.64° with unity-gain frequency of 12.95 kHz and 36° with unity-gain frequency of 16.4 kHz, respectively. A difference in phase margin of the LV and HV CMFB loop is due to the difference in capacitance of the upper and lower current driver halves.

Figure 12:
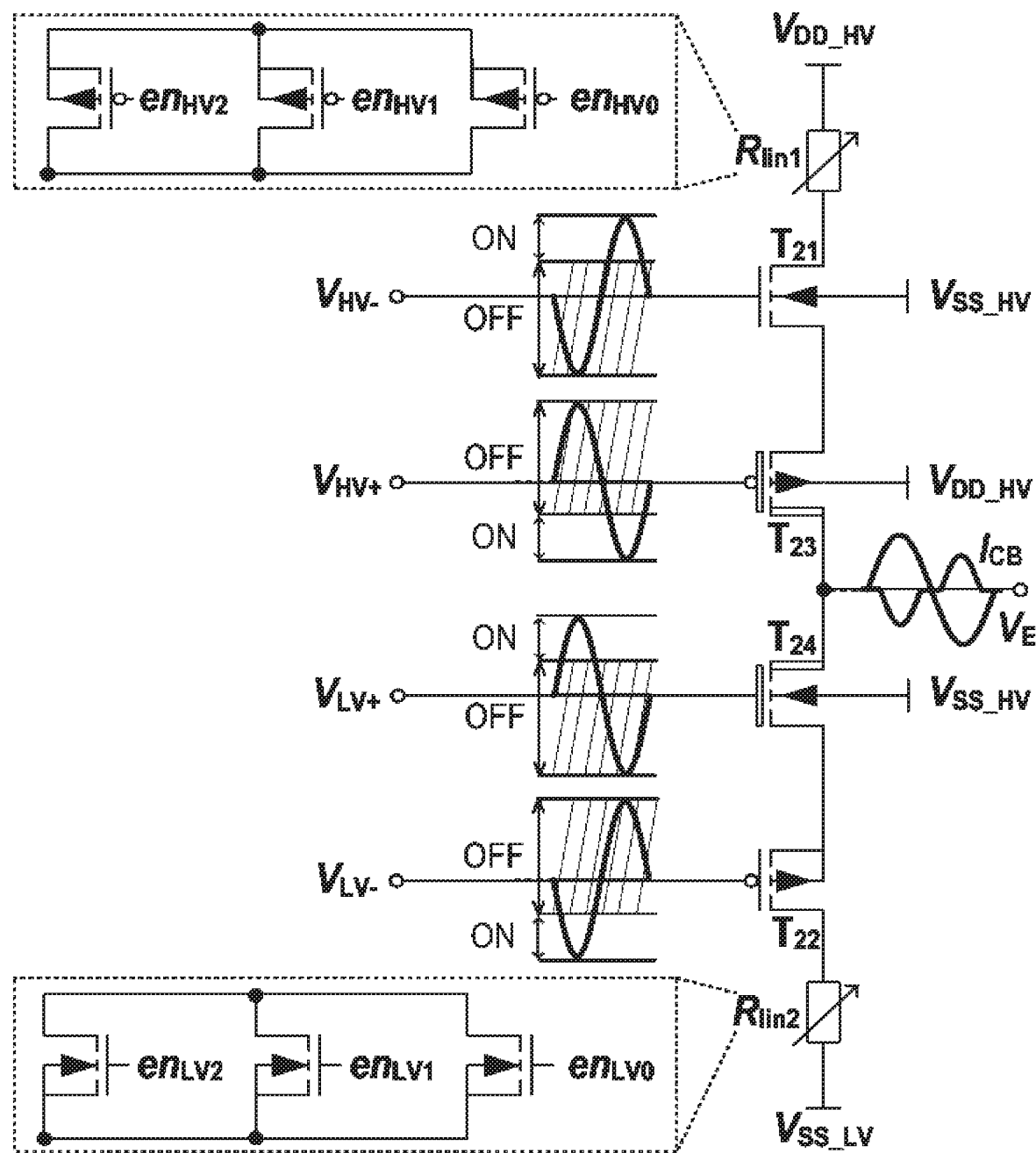
FIG. 12 shows an exemplary implementation of a compensation stage for a charge balancing circuit according to the improved concept.

FIG. 12 shows an exemplary implementation of a compensation stage CP for a charge balancing circuit CBC according to the improved concept. The compensation stage CP is implemented as a transistor stage with at least two transistor pairs $T_{21}$, $T_{22}$, $T_{23}$, $T_{24}$ connected in series. The current driver of the compensation stage CP is based on a class-B concept, modified by splitting the biasing of the intermediate transistors $T_{23}$, $T_{24}$ and translating it into the quad-rail domains. The gates of all four transistors are supplied by the outputs of the FDOTA. This guarantees that the difference between the gate voltages of upper and lower current driver does not exceed the $\Delta VLV$ subranges. The compensation current characteristic is thus independent of the overall HV environment. Another advantage of the presented current driver is that the bulk of the isolated LV transistor $T_{21}$ can be directly connected to its source. Therefore, the 22 V supply voltage restriction is increased to 40 V, now e.g. restricted by the maximum allowed gate-drain voltage of $T_{23}$ and $T_{24}$ in the used 0.35 μm HV process technology.

The working principle is illustrated for a varying $V_E$, highlighted in FIG. 12. If $V_E$ increases relative to $V_{CM}$, the gates of $T_{21}$, $T_{22}$ decrease, while the gates of $T_{23}$, $T_{24}$ increase. This results in the activation of the lower half, provided that the overhead voltage surpasses the sum of the threshold voltages of $T_{22}$, $T_{24}$. In this case, $I_{CB}$ compensates excess charges and decreases $V_E$ again. In the opposite case, when $V_E$ falls below the safety limit, the upper half is activated, sourcing current into the tissue to increase $V_E$, $I_{CB}$ changes quadratically with $V_E$ defined by $$I_{CB} = \frac{k}{2} \cdot (|V_E| \cdot A_{FDOTA} - (V_{t21,24} + |V_{t23,22}|))^2, \text{ with} \quad (5)$$

$$k = \beta_{21.23} \cdot \beta_{22,24} \cdot \frac{(\sqrt{\beta_{21.23}} + \sqrt{\beta_{22,24}})^2}{(\beta_{21.23} - \beta_{22,24})^2}, \quad (6)$$

with Vtxx being the threshold voltages of the respective transistors and with βxx being the gain factors of the respective transistors.

The intrinsic dead zone defines the safety limit, beyond which $I_{CB}$ is pushed into or pulled out of the nervous tissue. The allowed maximum $I_{CB}$ depends on the stimulation site and application. A method for current amplitude limitation without affecting the compensation gain is achieved by incorporating one or two linear resistances $R_{lin1,2}$ acting as current limiting components. For example, the configurable resistances $R_{lin1,2}$ are implemented by three transistors each, which simultaneously serve as switches, to select among three maximum current amplitudes.

It can be distinguished between consequence- and cause-based methods, since they differ in their mode of compensation. The consequence based approach aims for an instantaneous reduction of VE above the safety limit, after each stimulus. Cause-based methods try to adjust the charges of the anodic and cathodic stimulus, typically averaged over many pulses, ensuring long-term balanced conditions. Cause-based compensation is suitable for counteracting mismatch and process variations, but might show a settling process with overshoots during startup. The active charge balancer according to the improved concept eliminates excess charges instantaneously, based on its consequence-based compensation technique. Further, it offers a self-regulated and self-adaptive compensation by incorporating a dead zone, inherently by its class-B architecture. The circuit of all components can be designed to operate at different supply voltages by means of the quad-rail concept. The circuit may be designed and manufactured in a 0.35 μm HV CMOS process and verified by chip measurements. For such example, it is shown that the compensation current is independent of the supply voltage within the range of 6.6 to 38 V. Further the systems efficacy is unchanged at asymmetrically orientated supply rails with respect to the body's quiescent potential $V_{CM}$. Additional flexibility is given by two configurable safety limits, as well as three configurable maximum compensation current amplitudes. Due to the autonomous CB characteristic and the adaptive power supply compliance, the presented charge balancer provides high adaptability to various, even monophasic neural stimulators.

What is claimed is:

1. A charge balancing circuit adapted to be connected to an electrode and to a stimulation source, the stimulation source configured to provide a stimulus to the electrode for functional electrical stimulation of biological tissue, the charge balancing circuit comprising:
   an electrode terminal coupled to receive an electrode voltage;
   a reference terminal coupled to receive a reference voltage;
   a differential amplifier coupled to the electrode terminal and to the reference terminal, the differential amplifier being adapted to amplify and invert a difference between the electrode voltage and the reference voltage for generating a first pair of differential voltage signals and a second pair of differential voltage signals having a lower voltage level than the first pair of differential voltage signals; and
   a compensation stage implemented as a transistor stage with a plurality of transistor pairs connected in series between a first supply terminal and a second supply terminal, the compensation stage being configured to:
      generate, when the electrode voltage lies outside a specified safety range, an output current by controlling the transistor pairs with the first and the second pair of differential voltage signals; and
      supply the output current to the electrode terminal for driving the electrode voltage towards or into the specified safety range.

2. The charge balancing circuit according to claim 1, wherein the specified safety range is predetermined by threshold conditions of the transistor stage.

3. The charge balancing circuit according to claim 1, wherein the specified safety range is predetermined by a gain factor of a differential input stage of the differential amplifier.

4. The charge balancing circuit according to claim 1, wherein the transistor pairs of the compensation stage comprise:
   a first pair of transistors being implemented complementary to each other, being coupled in series and being controlled by the first pair of differential voltage signals; and
   a second pair of transistors being implemented complementary to each other, being coupled in series and being controlled by the second pair of differential voltage signals.

5. The charge balancing circuit according to claim 4, wherein the compensation stage comprises a current limiting component coupled in series with the first pair of transistors and the second pair of transistors.

6. The charge balancing circuit according to claim 1, wherein the first pair of differential voltage signals is in a voltage range of a first voltage domain, and the second pair of differential voltage signals is in a voltage range of a second voltage domain.

7. The charge balancing circuit according to claim 6, wherein the voltage range of the first voltage domain is higher than the voltage range of the second voltage domain.

8. The charge balancing circuit according to claim 6, wherein an upper boundary of the voltage range of the first voltage domain is defined by a potential at the first supply terminal, and a lower boundary of the voltage range of the second voltage domain is defined by a potential at the second supply terminal.

9. The charge balancing circuit according to claim 1, wherein the differential amplifier comprises:
   a differential input stage configured to generate an amplified difference signal based on the difference between the electrode voltage and the reference voltage;
   a level translator stage configured to generate a level shifted difference signal from the amplified difference signal;
   a first output stage configured to generate the first pair of differential voltage signals from the level shifted difference signal; and
   a second output stage configured to generate the second pair of differential voltage signals from the amplified difference signal.

10. The charge balancing circuit according to claim 1, further comprising a switch arrangement configured to:
    connect the differential amplifier to the electrode terminal during an operating mode of operation of the charge balancing circuit; and
    disconnect the differential amplifier from the electrode terminal during a pause mode of operation of the charge balancing circuit.

11. A stimulator circuit for functional electrical stimulation, the stimulator circuit comprising:
    an electrode terminal coupled to receive an electrode voltage;
    a reference terminal coupled to receive a reference voltage;

a charge balancing circuit comprising a differential amplifier coupled to the electrode terminal and to the reference terminal; and a stimulation source connected to the electrode terminal, wherein the stimulation source is implemented as a current source and is configured to supply a monophasic or a biphasic current pulse to the charge balancing circuit via the electrode terminal, wherein the differential amplifier is configured to amplify and invert a difference between the electrode voltage and the reference voltage for generating a first pair of differential voltage signals and a second pair of differential voltage signals having a lower voltage level than the first pair of differential voltage signals, and wherein the charge balancing circuit further comprises a compensation stage implemented as a transistor stage with a plurality of transistor pairs connected in series between a first supply terminal and a second supply terminal, the compensation stage being configured to:

generate, when the electrode voltage lies outside a specified safety range, an output current by controlling the transistor pairs with the first and the second pair of differential voltage signals; and supply the output current to the electrode terminal for driving the electrode voltage towards or into the specified safety range.

12. The stimulator circuit according to claim 11, wherein the specified safety range is predetermined by threshold conditions of the transistor stage.

13. The stimulator circuit according to claim 11, wherein the specified safety range is predetermined by a gain factor of a differential input stage of the differential amplifier.

14. The stimulator circuit according to claim 11, wherein the current source is connected to the first supply terminal for supplying current of a first polarity to form a first part of the current pulse.

15. The stimulator circuit according to claim 11, wherein the current source is connected to the second supply terminal for supplying current of a second polarity to form a second part of the current pulse.

16. A method for charge balancing for functional electrical stimulation of biological tissue, the method comprising:

receiving an electrode voltage;

receiving a reference voltage;

generating a first pair of differential voltage signals and a second pair of differential voltage signals having a lower voltage level than the first pair of differential voltage signals by amplifying and inverting a difference between the electrode voltage and the reference voltage;

determining that the electrode voltage lies outside a specified safety range; and generating, depending on the first and the second pair of differential voltage signals, an output current for driving the electrode voltage towards or into the specified safety range by controlling a plurality of transistor pairs connected in series between a first and a second supply terminal.

17. The method according to claim 16, wherein the specified safety range is predetermined by threshold conditions of the plurality of transistor pairs.

18. The method according to claim 16, wherein the specified safety range is predetermined by a gain factor of the amplification of the difference between the electrode voltage and the reference voltage.

* * * * *